United States Patent
Goodwill

(10) Patent No.: US 10,466,316 B2
(45) Date of Patent: Nov. 5, 2019

(54) MAGNETIC PARTICLE IMAGING

(71) Applicant: MAGNETIC INSIGHT, INC., Alameda, CA (US)

(72) Inventor: Patrick W. Goodwill, Oakland, CA (US)

(73) Assignee: MAGNETIC INSIGHT, INC., Alameda, CA (US)

(*) Notice: Subject to any disclaimer, the term of this patent is extended or adjusted under 35 U.S.C. 154(b) by 0 days.

(21) Appl. No.: 15/648,421

(22) Filed: Jul. 12, 2017

(65) Prior Publication Data
US 2018/0017641 A1    Jan. 18, 2018

Related U.S. Application Data

(60) Provisional application No. 62/361,475, filed on Jul. 12, 2016, provisional application No. 62/361,463, filed on Jul. 12, 2016.

(51) Int. Cl.
| | |
|---|---|
| *G01R 33/12* | (2006.01) |
| *A61B 5/05* | (2006.01) |
| *G01N 27/72* | (2006.01) |
| *G01R 33/02* | (2006.01) |
| *G01R 33/10* | (2006.01) |

(52) U.S. Cl.
CPC ........ *G01R 33/1276* (2013.01); *A61B 5/0515* (2013.01); *G01N 27/72* (2013.01); *G01R 33/0213* (2013.01); *G01R 33/10* (2013.01)

(58) Field of Classification Search
CPC ............ G01R 33/1276; G01R 33/0213; G01R 33/10; G01N 27/72; A61B 5/0515
See application file for complete search history.

(56) References Cited

U.S. PATENT DOCUMENTS

| | | | |
|---|---|---|---|
| 4,538,130 A | 8/1985 | Gluckstern | |
| 4,545,384 A | 10/1985 | Kawachi | |
| 5,004,983 A | 4/1991 | Proksa | |
| 5,510,711 A | 4/1996 | Molyneaux | |
| 7,778,681 B2 * | 8/2010 | Gleich | ............... A61B 5/0515 324/300 |
| 8,847,592 B2 | 9/2014 | Goodwill | |
| 8,884,617 B2 | 11/2014 | Goodwill | |
| 9,274,084 B2 | 3/2016 | Goodwill | |

(Continued)

FOREIGN PATENT DOCUMENTS

| | | |
|---|---|---|
| EP | 2547253 | 1/2013 |
| EP | 3143929 | 3/2017 |

(Continued)

OTHER PUBLICATIONS

U.S. Appl. No. 15/674,234, filed Aug. 10, 2017, Goodwill Patrick W.

(Continued)

*Primary Examiner* — Gregory H Curran
(74) *Attorney, Agent, or Firm* — Pillsbury Winthrop Shaw Pittman LLP

(57) ABSTRACT

A Magnetic Particle Imaging (MPI) system including a mechanically-rotatable magnet generating a field-free line, where the system is capable of acquiring a plurality of projections at a plurality of rotation angles, and where the projection acquisition includes positioning the field free line at a plurality of positions at the plurality of angles.

22 Claims, 24 Drawing Sheets

(56) References Cited

U.S. PATENT DOCUMENTS

| | | | |
|---|---|---|---|
| 9,763,594 | B2 | 9/2017 | Goodwill |
| 2003/0085703 | A1 | 5/2003 | Gleich |
| 2005/0073309 | A1 | 4/2005 | Williams |
| 2006/0211938 | A1 | 9/2006 | Gleich |
| 2006/0248944 | A1 | 11/2006 | Gleich |
| 2007/0258908 | A1 | 11/2007 | Lanza |
| 2008/0218162 | A1 | 9/2008 | Ruhrig |
| 2008/0309330 | A1 | 12/2008 | Ohyu |
| 2009/0115415 | A1 | 5/2009 | Weaver |
| 2010/0033171 | A1 | 2/2010 | Gleich |
| 2010/0052668 | A1 | 3/2010 | Gleich |
| 2012/0065491 | A1 | 3/2012 | Borgert |
| 2014/0159712 | A1 | 6/2014 | Graziani |
| 2014/0306698 | A1 | 10/2014 | Bontus |
| 2015/0008910 | A1 | 1/2015 | Goodwill |
| 2015/0316628 | A1 | 11/2015 | Heidenreich |
| 2018/0017639 | A1 | 1/2018 | Goodwill |
| 2018/0017640 | A1 | 1/2018 | Goodwill |

FOREIGN PATENT DOCUMENTS

| | | |
|---|---|---|
| WO | 2004091395 | 10/2004 |
| WO | 2008099331 | 8/2008 |
| WO | 2010008478 | 1/2010 |
| WO | 2011010243 | 1/2011 |
| WO | 2011116229 | 9/2011 |

OTHER PUBLICATIONS

Biederer, S et al.; "A Spectrometer for Magnetic Particle Imaging," IFMBE Proceedings (International Federation for Medical and Biological Engineering), Springer, DE, vol. 22, No. 3, Feb. 4, 2009, pp. 2313-2316, XP009130408, ISSN: 1680-0737, DOI: 10.1007/978-3-540-89208-3_555.

EP App. No. 16173404.1; European Search Report and Written Opinion dated Jan. 25, 2017.

Gleich et al., Tomographic imaging using the nonlinear response of magnetic particles, Nature, 435(7046): 1214-7, Jun. 2005.

Goodwill and Conolly; Multidimensional x-space Magnetic Particle imaging, IEEE Transactions on Medical Imaging, 30(9): (2011) 1581-1590, ISSN 1558-254X.

Goodwill, Narrowband and x-Space Magnetic Particle Imaging, dissertation, 2010.

Knopp et al., Trajectory analysis for magnetic particle imaging, Dec. 2008, p. 386.

Konkle, J J et al.; "Twenty-fold acceleration of 3D projection reconstruction MPI", Biomedizinische Technik Walter De Gruyter Germany, vol. 58. No. 6. , Dec. 2013 (Dec. 2013), pp. 565-576, XP002773942, ISSN: 0013-5585.

Kovács, Attila, "Scanning strategies for imaging arrays," Proc. SPIE 7020, Millimeter and Submillimeter Detectors and Instrumentation for Astronomy IV, 702007 (Jul. 18, 2008); doi: 10.1117/12.790272.

PCT App. No. PCT/US2009/003764; Preliminary Report on Patentability Chapter I dated Jan. 5, 2011.

PCT App. No. PCT/US2009/003764; International Search Report and Written Opinion dated Jan. 15, 2010.

PCT App. No. PCT/US2011/028879; International Search Report and Written Opinion dated Oct. 19, 2011.

PCT App. No. PCT/US2011/028879; Preliminary Report on Patentability Chapter I dated Sep. 18, 2012.

PCT App. No. PCT/US2017/041783; International Search Report and Written Opinion dated Nov. 21, 2017.

PCT App. No. PCT/US2017/041792; International Search Report and Written Opinion dated Oct. 16, 2017.

Weber, Matthias et al.; "MPI with a mechanically rotated FFL", 2015 5th International Workshop on Magnetic Particle Imaging (IWMPI), IEEE, Mar. 26, 2015 (Mar. 26, 2015), p. 1, XP032776021, DOI: 10.1109/IWMPI.2015.7107026, ISBN: 978-1-4799-7269-2.

* cited by examiner

MAGNETIC PARTICLE IMAGING

CROSS-REFERENCE TO RELATED APPLICATIONS

The current application claims priority under 35 U.S.C. § 119 to U.S. Provisional Patent Application No. 62/361,475 filed Jul. 12, 2016 and titled "MAGNETIC PARTICLE IMAGING," and to U.S. Provisional Patent Application No. 62/361,463 filed Jul. 12, 2016 and titled "MAGNETIC PARTICLE IMAGING," the contents of which are hereby incorporated by reference in their entirety.

STATEMENT REGARDING FEDERALLY SPONSORED RESEARCH OR DEVELOPMENT

This invention was made with government support under grant numbers 1R43DA041814 and 1R43EB020463 awarded by the National Institutes of Health. The government has certain rights in the invention.

BACKGROUND

Magnetic particle imaging (MPI) is a technique allowing for the detection of certain nanoparticles and may be used, for example, in diagnostic imaging applications. Imaging may be facilitated through magnets designed to create a Field-Free Region (FFR). Examples of field free regions include a Field Free Point (FFP) and a Field Free Line (FFL).

SUMMARY

A Magnetic Particle Imaging (MPI) system is disclosed. Some implementations can include a mechanically-rotatable magnet configured to generate a magnetic field including a field-free line. Other implementations may include an excitation source and an RF detector. Implementations of the MPI system can include a control system configured to acquire projections at a number of angles. Acquiring the projections can include rotating the mechanically-rotatable magnet to orient the field free line at the angles. The field free line can be positioned at a number of positions and angles. The excitation source and RF detector can be controlled to acquire signals from magnetic particles in a sample within the field free line at the positions. The image reconstruction system can be configured to generate an image based at least on the projections.

In some variations, positioning the field free line at the positions can occur with the mechanically-rotatable magnet fixed at an angle. The image reconstruction system can be further configured to create the image from projections acquired at a fixed angle. The image reconstruction system can also be configured to generate a three-dimensional image.

In other variations, positioning the field free line at the positions can occur while the mechanically-rotatable magnet is rotating. The mechanically-rotatable magnet can include reversing rotation direction during acquisition of the projections.

In some variations, the control system can be further configured to move the sample through a bore of the mechanically-rotatable magnet during the acquiring or to move the sample through a bore of the mechanically-rotatable magnet, acquire additional projections at other angles, and the image reconstruction system can be configured to generate a three-dimensional image.

In other variations, control system can be further configured to electronically move the free field line along a rotation axis of the mechanically-rotatable magnet, acquire additional projections at another plurality of angles, or be configured to generate a three-dimensional image. Positioning the field free line at the positions can be accomplished at least by the mechanically-rotatable magnet generating a modified magnetic field.

In yet other implementations, positioning the field free line at the positions can include varying the position of the field free line only in the X direction with a shifting magnet and an excitation magnet.

In some variations, positioning the field free line in positions includes varying the position of the field free line in both the X direction and in the Z direction with at least one magnet and with at least one excitation magnet.

In other variations, the MPI system can include a shim magnet configured to alter the magnetic field, where alteration of the magnetic field can cause a widening of the field free line.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

An MPI system can be used to image tracer particles that may be present in an object, for example, in the anatomy of a person or animal. An MPI system can image tracer particles by causing them to emit electromagnetic radiation in response to a locally changing magnetic field. The change in the magnetic field can result from changes in an externally applied magnetic field, from movement of the tracer particles, or a combination of the two.

In many implementations, an MPI system will produce magnetic fields that include a field-free region or magnetic null. Tracer particles present in an object can change the orientation of their magnetic moment as they pass through such a region and the magnetic field changes from being oriented in a one direction to being oriented in another direction. Alternatively, tracer particles can be caused to change their orientation while in a field free region by a separate electromagnetic pulse.

MPI systems typically include a detector configured to detect the electromagnetic radiation from tracer particles, or detect the changes in magnetic flux that result from tracer particles responding to changes in the magnetic field or moving through the magnetic field. This electromagnetic signal can be used to generate an image of the tracer particles located within an imaging volume.

Some implementations of magnetic particle imaging can include moving the object to be imaged, moving the location of the field-free region, or a combination of the two.

The distribution of tracer particles imaged in a subject can be related to particular anatomical features or physical structures of the object (e.g., particles accumulated in a cavity or blood vessel) or to a distribution of elements in the object that the tracer particles have attached to (e.g., a particular molecule, cell or tissue type that has a propensity to preferentially bond with the tracer particles or molecules that the tracer particles have been attached to or contained within). In this way, the determined location of the tracer particles can be used to image features inside the object.

Figure 1:
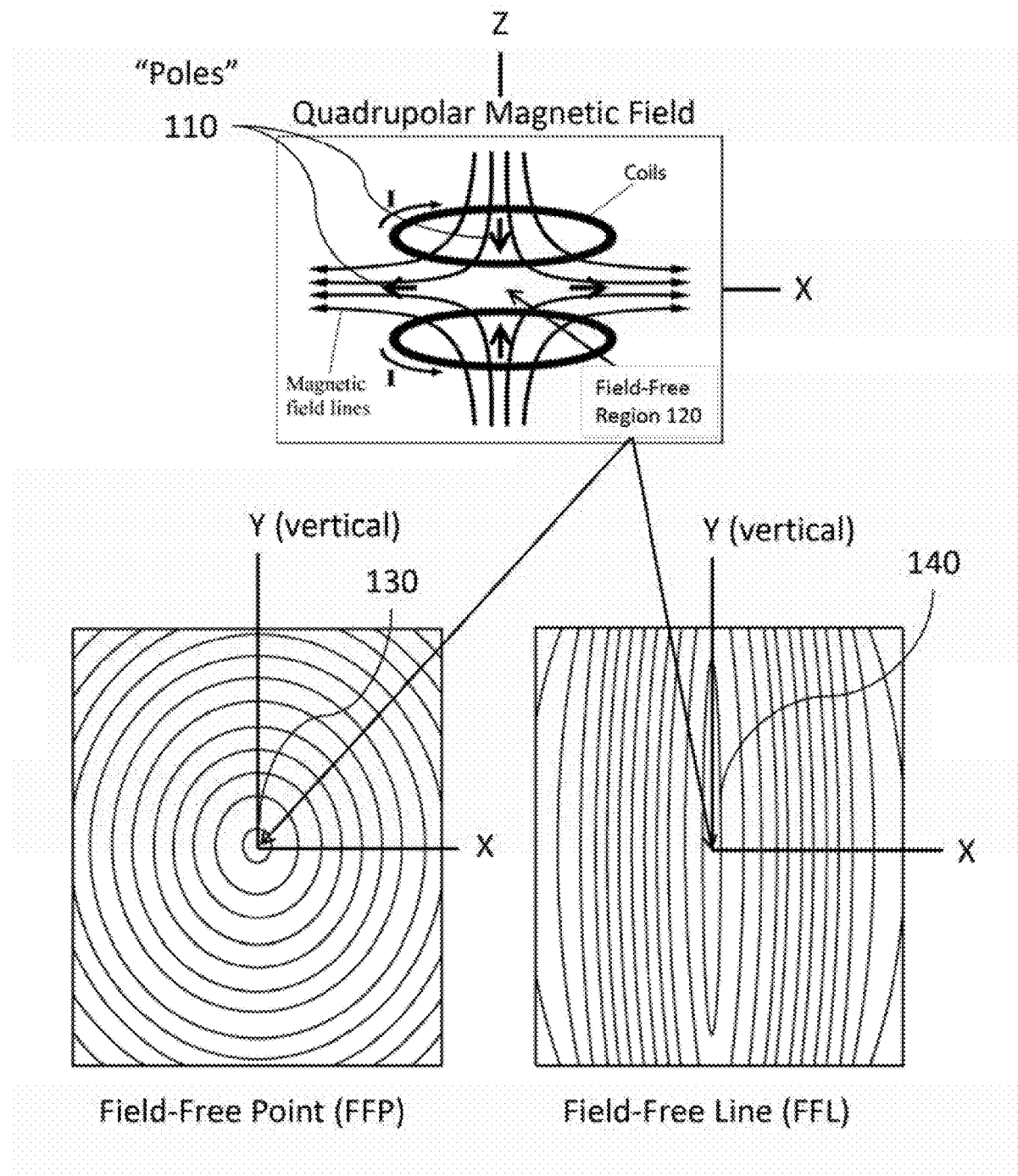
FIG. 1 is a diagram illustrating a quadrupolar magnetic field, a FFP, and a FFL, in accordance with certain aspects of the present disclosure.

FIG. 1 is a diagram illustrating a quadrupolar magnetic field, a FFP 130, and a FFL 140, in accordance with certain aspects of the present disclosure. An MPI system can produce a quadrupolar magnetic field (upper part of FIG. 1) that contains a magnetic null, zero-point or field-free region 120. In the simplified example of FIG. 1, two coils with currents traveling in opposite directions are generating a quadrupolar magnetic field. The four "poles" 110 of the quadrupolar magnetic field are shown by the short arrows. The poles 110 are provided as examples of a magnetic configuration equivalent to the two opposed coils shown in FIG. 1. The poles 110 are located between the two coils in the case where the currents in the coils are equal and opposite.

In some implementations, the field-free region 120 can be a FFP 130 (as shown by the simplified illustration in the lower left half of FIG. 1). In other implementations, the field-free region can take the form of a field free line 140 (as shown by the simplified illustration in the lower right half of FIG. 1). The Y-axis of the plots in FIG. 1 are labeled as vertical to be consistent with later figures, showing the typically vertical orientation of field-free line 140. When an MPI system is configured to generate a field-free line 140, the MPI signal is received from the line, instead of from a point. FFL configurations may thus utilize projection-based imaging and reconstruction techniques.

Field-free line 140 is a generally elongate region, having a length and a thickness, where the magnetic field is significantly lower than at other locations in the magnetic field generated by the MPI system. As used herein, a "field-free line" is understood to account for the reality that the line may not be perfectly straight, nor completely absent magnetic field, but that such is generally the goal of an FFL.

The field-free line 140 can, in some implementations, be generally elongate or "linear" only within an imaging volume of the MPI system. It is less important for the FFL to maintain linearity outside the imaging volume and thus field-free line 140 may deviate to a different shape away from its center, proximate the center of the imaging volume. Similarly, as used herein, a "field-free point" refers to an approximately spherical region of low magnetic field.

Figure 2:
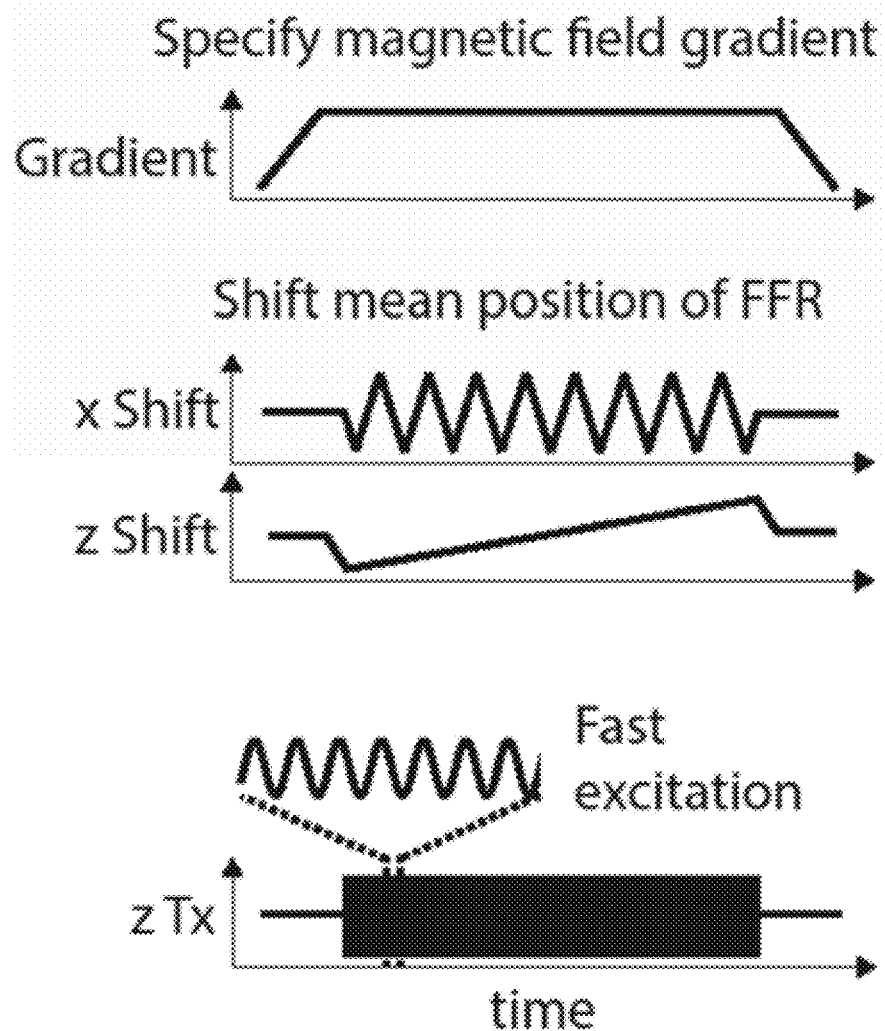
FIG. 2 is a diagram illustrating an exemplary pulse sequence for moving a FFL in accordance with certain aspects of the present disclosure.

FIG. 2 is a diagram illustrating an exemplary pulse sequence for moving a FFL 140 in accordance with certain aspects of the present disclosure. To generate an image, FFL 140 can be moved to scan different positions in an imaging volume (e.g., around a sample). To move FFL 140, the MPI system can implement a pulse sequence. A pulse sequence is a set of actions performed by the MPI scanning hardware. The pulse sequence can be designed to image a desired Field of View (FOV) through, for example, movement of FFL 140, movement of the sample 410, movement of the MPI system, or any combination of the above.

The example pulse sequence illustrated in FIG. 2, includes specifying a magnetic field gradient (shown in the top panel of FIG. 2), electronic movement of FFL 140 to cover the field of view (shown in the middle two panels of FIG. 2), and fast electronic movement of FFL 140 by an excitation magnet or coil to induce a signal from the sample (shown in the bottom panel of FIG. 2).

In other implementations, the pulse sequence can further include controlling mechanical movement of the sample, movement or rotation of the MPI system, setting an excitation field vector (strength and direction of the magnetic field generated by the excitation magnet or coil), specifying a number and value of angles, or any combination thereof.

These actions can be implemented through computer controlled changing of currents in MPI magnets, changing currents in the drive field magnets, and mechanical movement of the MPI system using motors. During the pulse sequence, data acquisition can occur during application of the drive field. Image reconstruction can then be based on the specifics of the pulse sequence (i.e., applied currents and mechanical positions) with the received signal to produce an image.

Figure 3:
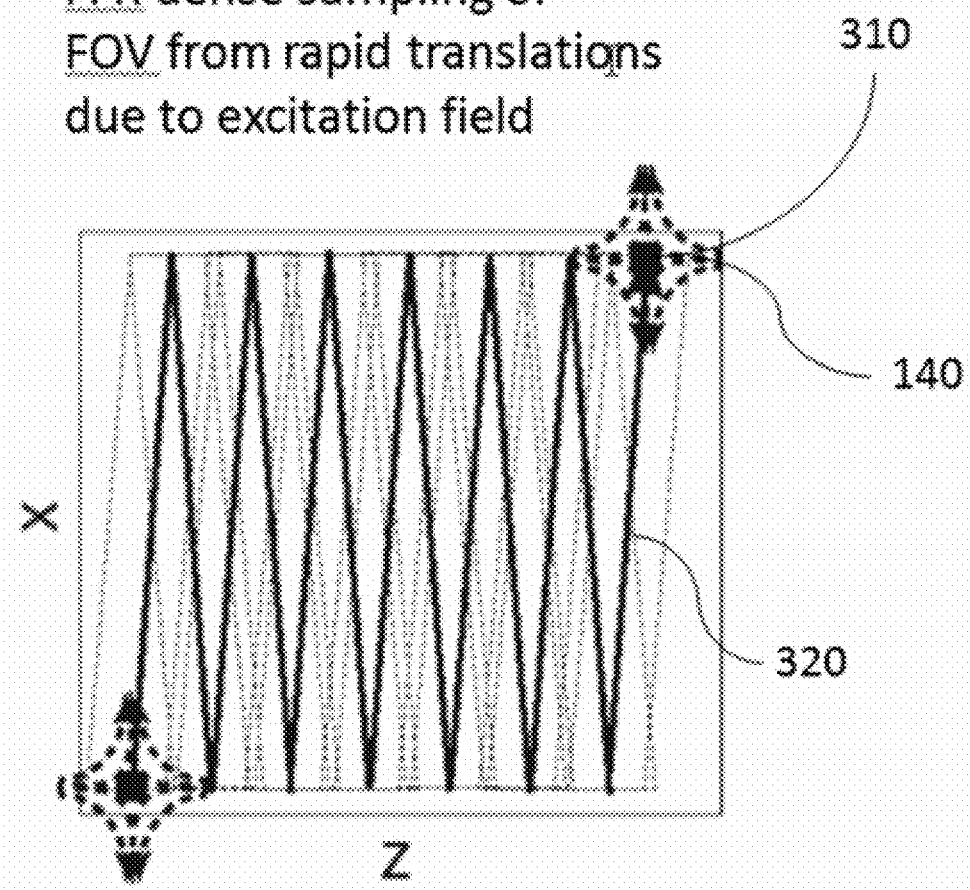
FIG. 3 is a diagram illustrating movement of a FFL along a trajectory during imaging in accordance with certain aspects of the present disclosure.

FIG. 3 is a diagram illustrating movement of a FFL 140 along a trajectory 320 during imaging in accordance with certain aspects of the present disclosure. The position 310 of FFL 140 can be varied by the combination of magnets in the MPI system by generating a modified magnetic field relative to the quadrupolar field illustrated in FIG. 1. These magnets can include, for example, main magnets or "X magnets" that are configured to generate the FFL 140 and control the X position 310 of FFL 140, shifting magnets or "Z magnets" that are configured to modify or control the gradients around FFL 140 and also shift the Z position 310 of FFL 140. An example of the slow variation in position 310 of FFL 140 is illustrated by the zig-zag path in FIG. 3. Here, FFL 140 is moving back and forth in the X direction while generally moving in the Z direction.

Also, the MPI system can include excitation magnets configured to generate rapid variations in, for example, the X or Z positions of FFL 140 and to excite the particle tracers to generate signal. The example shown in FIG. 3 shows that the excitation magnet (driven to move FFL 140 rapidly over a short distance in the Z direction) causes a dense sampling of the scanned imaging area around the slow path created through the X and Z magnets.

Depending on the choice of magnets used to vary the position 310 of FFL 140, an image of a "slice" of the imaging volume can be acquired, or a "slab" of the imaging volume can be acquired. As used herein, a "slice" is generally a two-dimensional imaging region of significantly smaller thickness than a "slab." For example, positioning FFL 140 can include varying the position 310 of FFL 140 only in one direction (e.g., the X direction) with a shifting magnet and an excitation magnet. In this example, because there is no variation in an orthogonal direction (e.g., the Z direction), FFL 140 sweeps out a thin slice.

Figure 4:
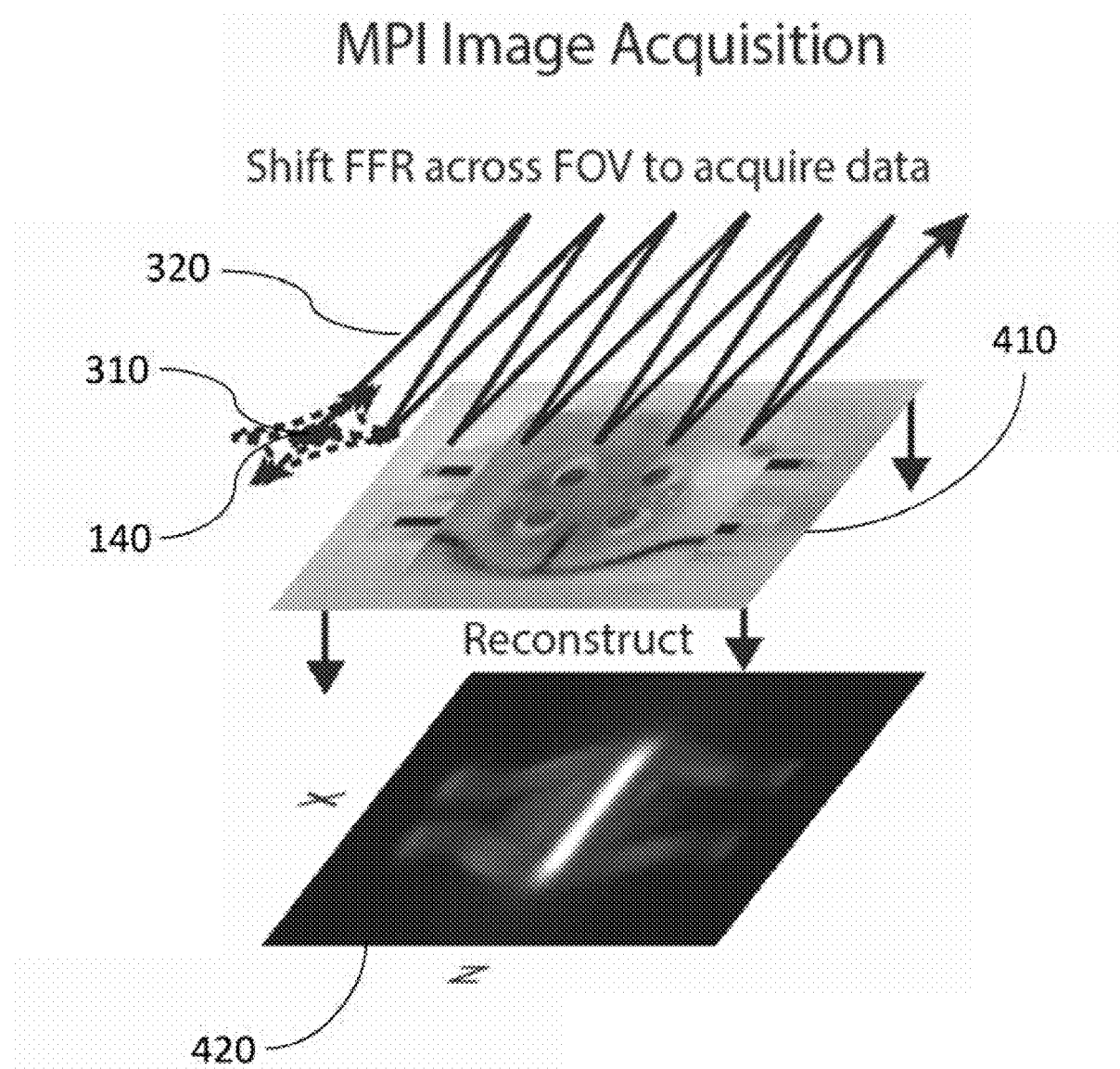
FIG. 4 is a diagram illustrating scanning of a sample with FFL movement in two dimensions to generate an image in accordance with certain aspects of the present disclosure.

A slab can be imaged when positioning the FFL 140 includes varying the position of the field free line in both directions orthogonal to the axis of FFL 140 (e.g., varying in both the X direction and in the Z direction). As shown in FIG. 4, the position 310 of FFL 140 can be varied slowly with, for example, the X magnets and Z magnets. In addition, the excitation magnets (that rapidly move the position 310 of FFL 140 in the X or Z directions) can also add some nominal thickness to the volume imaged with FFL 140.

The specifics of FFL 140 trajectory 320 can change depending on the excitation magnetic field vector. For example, an excitation field in Z can cover the field of view when rapidly shifted in the X direction. Likewise, an excitation field in the X direction can cover the field of view when rapidly in shifted in the Z direction. In some implementations, an excitation field can be produced in both the X and Z directions.

FIG. 4 is a diagram illustrating scanning sample 410 with FFL 140 in two dimensions to generate image 420 in accordance with certain aspects of the present disclosure. "Projections," which as used herein refer to a signal detected from electromagnetic radiation emitted by the tracer particles in FFL 140, can be used to reconstruct an image 420 of the tracer particle distribution in sample 410. At each position 310 of FFL 140, a projection is generated based on signals from the tracer particles in FFL 140.

As shown in the top portion of FIG. 4, in some implementations, FFL 140 can be moved across sample 410 rapidly along one axis (e.g., the X axis), and slowly along a second axis (e.g., the Z axis). In other implementations, scanning trajectories such as spirals (e.g., where FFL 140 is moved in a spiral pattern in the X-Z plane) and Cartesian grids (e.g., where FFL 140 is moved along X only, and then a short distance along Z, and then back along X in the opposite direction, and so on until a grid-like pattern is formed) are possible. With a sufficient number of projections, image 420 (2D as shown, or 3D in other implementations) can be reconstructed, for example by X-space reconstruction, tomographic methods, etc.

The number of projections can range from just a few for sparse datasets, to 50 or even a 500+ depending on the level of undersampling or oversampling desired, the strength of the magnetic field gradient, and the tracer particle used. In other implementations, projections can also be acquired using the mechanical movement of the sample 410.

Figure 5:
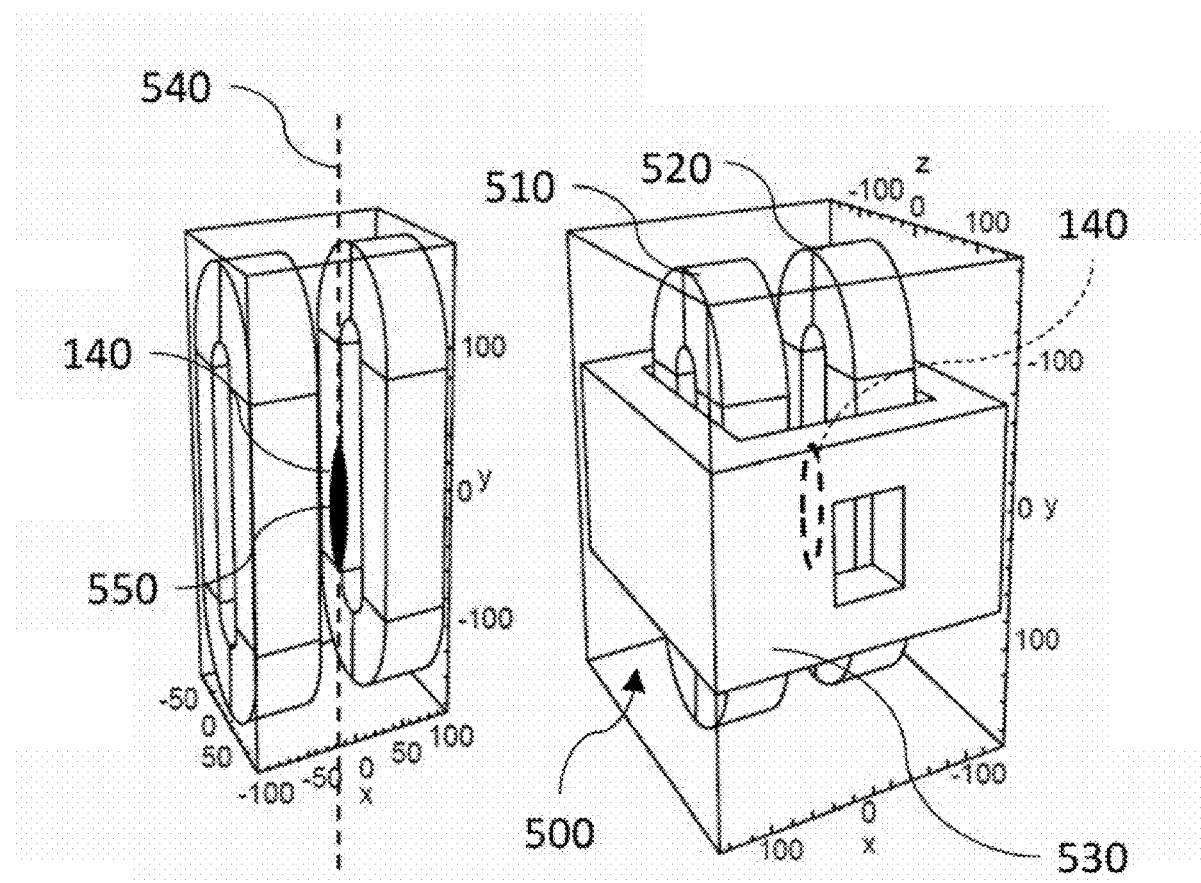
FIG. 5 is a diagram illustrating a simplified MPI system in accordance with certain aspects of the present disclosure.

FIG. 5 is a diagram illustrating a simplified MPI system in accordance with certain aspects of the present disclosure.

As shown in FIG. 5, MPI system 500 can include two magnets 510, 520. For example, when the magnets 510, 520 have opposing currents, they can generate a quadrupolar magnetic field that includes FFL 140, similar to the example in FIG. 1. FFL 140 can have an FFL axis 540 extending along the length of FFL 140 and passing through FFL center 550 of FFL 140. In the exemplary design shown in FIG. 5, the magnet includes a first magnet 510 and a second magnet 520. The present disclosure, however, contemplates that the requisite magnetic field and field free line may be generated by any number, and any type, of magnets. For example, the magnet may incorporate multiple magnets (2, 3, 4, etc.) and such magnets can be, for example, a permanent magnet, a current-carrying coil or electromagnet, an electromagnet with a flux return, or any combination of such magnets. The magnet may in fact be only a single magnet, to the extent such is capable of generating a field free line (for example, a Halbach cylinder). The discussion of the exemplary magnet design herein including two main magnets is not intended to be limiting.

Some implementations of MPI system 500 can include two or more high-power, water-cooled electromagnets, and two shim magnets (although fewer or more than two shim magnets can be used). Shim magnets can alter the magnetic field, for example to cause a shortening of FFL 140.

In other implementations, the magnets 510, 520 can be elongate. As used herein, the term "elongate" refers to a geometry where the magnets are longer in one dimension then in another (i.e., not a circular coil). The length of such an elongate configuration can determine, in part, the length of FFL 140.

MPI systems, as described herein, can include an excitation source, an RF detector, and a control system configured to acquire projections according to any of the methods described herein. An excitation source can include any type of RF generator, for example, one or more coils or transmit coils, antennas, waveguides that supply RF to FFL 140, and the like. A control system can include any combination of hardware and software that is configured to control the operation of the magnets, rotation drivers for the mechanically-rotatable magnet 610, RF receivers or receive coils, and the like. Any of the components of the control system can be configured to work together to enable the methods, mechanical operations, and software operations described herein. The control system can also execute pulse sequences, as described herein.

FIG. 5 also shows a flux return 530 integrated with the first and second magnets 510 and 520. As used herein, "flux return" refers to any arrangement of material components that shape the magnetic flux in the manner described herein. The flux return 530 may contain, for example, a ferromagnetic material such as iron, or any other material having a low reluctance compared to other materials, such as air, to more efficiently channel, guide, shape, or concentrate magnetic flux. The flux return 530 can be, for example, in two halves, or a number of layers of laminates that can be stacked or otherwise assembled to form flux return 530.

The simplified diagram in FIG. 5 also shows a square aperture in the flux return 530 surrounding the magnets. This aperture can be aligned with the imaging region (or bore) to allow access to the field-free region through the flux return 530.

Figure 6:
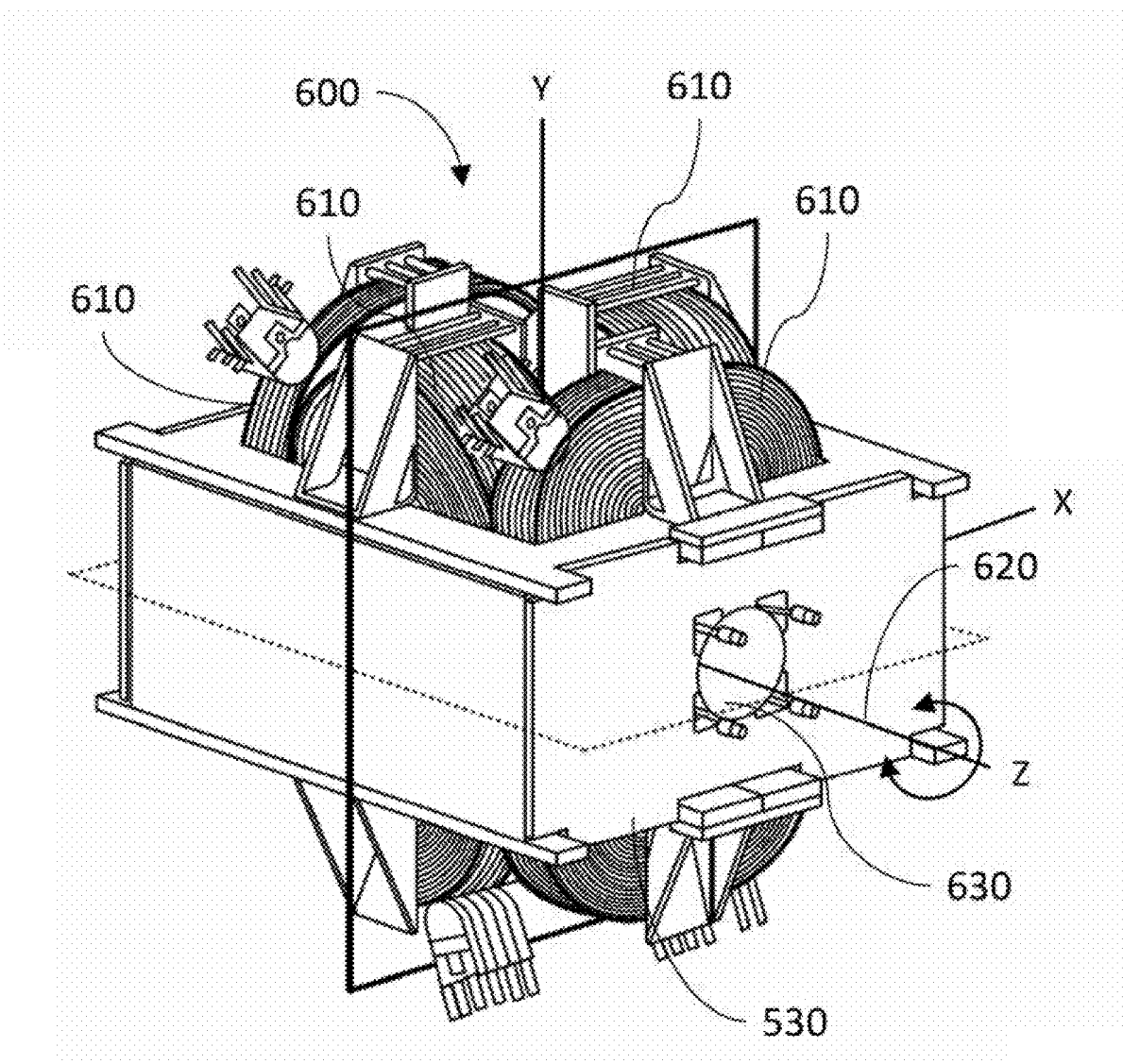
FIG. 6 is a diagram illustrating an example of a MPI system in accordance with certain aspects of the present disclosure.

FIG. 6 is a diagram illustrating an MPI system 600 in accordance with certain aspects of the present disclosure.

Rotating MPI system 600 includes a mechanically-rotatable magnet 610 that can generate a magnetic field that includes FFL 140 for imaging a sample 410. However, with mechanically-rotatable magnet 610, projections can be acquired at different angles through mechanical rotation.

Similar to a stationary MPI system, the image reconstruction system can be configured to generate a two dimensional image or a three dimensional image. Image reconstruction systems can generate an image resolved in all three dimensions based on the projections acquired at different angles. However, with a mechanically-rotatable magnet 610, because projections are acquired at different angles, data acquisition and reconstruction methods can be used that differ from data acquisition and reconstruction with a stationary MPI system. With a mechanically-rotatable magnet 610, many of the MPI operations described previously can still be performed. For example, the magnets can position the field free line at least by the mechanically-rotatable magnet 610 (e.g., a Z magnet, X magnet, shim magnet, or excitation magnet).

MPI system 600 is similar to MPI system 500, however MPI system 600 includes components (such as mechanically-rotatable magnets 610) configured to rotate about rotation axis 620. As shown in FIG. 6, MPI system 600 also includes bore 630 that can receive the object that is to be imaged. FFL 140 can extend perpendicularly (here along the Y axis) to the bore 630 (here along the Z axis) though, as described herein, FFL 140 can be shifted in any direction by the application of additional magnetic fields. In some implementations, MPI system 600 can rotate about rotation axis 620 of the bore 630.

The present disclosure contemplates that some components of MPI system 600 can rotate about one or more axes of rotation. When the present disclosure refers to "MPI system 600," this refers to any portion of rotatable MPI system 600 that is constructed to rotate around rotation axis 620, and does not imply that every component of MPI system 600 is configured to (or must) rotate to enable the disclosed methods. The components of MPI system that can be configured to rotate can include, for example, some or all of the magnets (e.g., main magnets, shifting magnets, shim magnets, excitation magnets), passive shims, flux return, detectors, shielding, cables, a gantry or other support system for any of the above, or any combination the above.

As used herein, a "rotation axis 620" refers to any axis that any part of MPI system 600 is configured to rotate about. For example, as shown in FIG. 3, the first magnet 510 and the second magnet 520 and the flux return 530 are shown as capable of rotating about the rotation axis 620, which in this case is the z-axis that extends along the center of the length of the bore 630. In other implementations, MPI system 600 can rotate about other axes, which may or may not be an orthogonal X, Y, or Z-axis as shown in FIG. 6. When MPI system 600 rotates about rotation axis 620 (e.g., the Z-axis), it is understood that the coordinate system (taken to be in the frame of reference of the MPI system 600 and not a lab frame of reference) correspondingly rotates (e.g., the X axis and Y axis rotate with MPI system 600).

In one implementation, the gantry can be directly driven with a direct drive motor. This approach allows accurate control of the magnet position 310. The choice of a direct drive motor can be costly, however, and may require the use of a unique motor when requiring a large access hole through the gantry for hoses and current carrying conductors.

Figure 7:
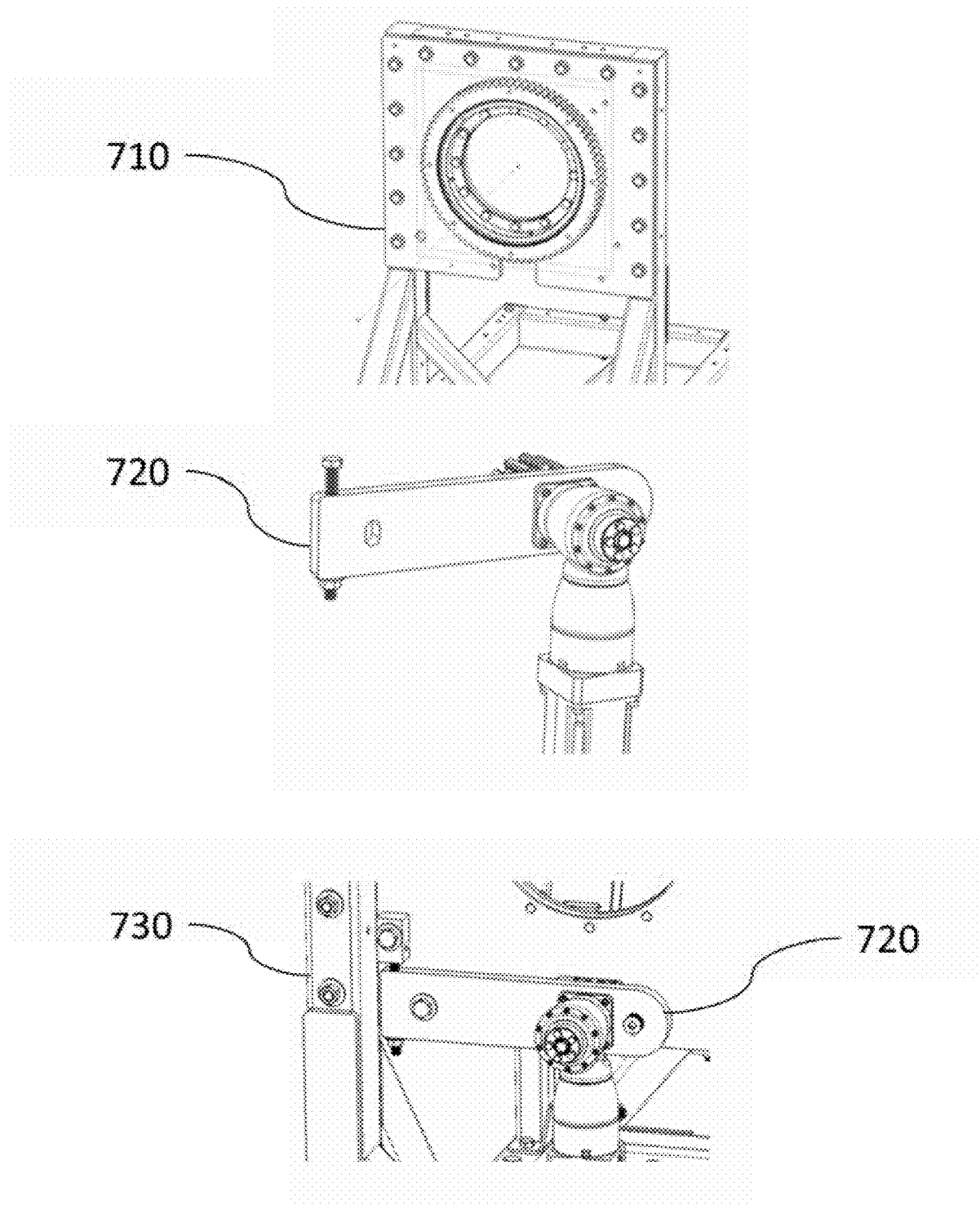
FIG. 7 is a diagram illustrating pinions and gears for direct drive of a MPI system in accordance with certain aspects of the present disclosure.

FIG. 7 is a diagram illustrating pinions and gears for direct drive of an MPI system in accordance with certain aspects of the present disclosure. The top portion of FIG. 7 shows attachment of the magnet bearing assembly. The middle portion of FIG. 7 shows a pinion, gearbox, and servo motor mounted to a backlash adjustment lever arm. The bottom portion of FIG. 7 shows a motor and pinion assembly mounted to the frame. In some implementations, the pinion to drive a gear tooth approach may be used to rotate MPI system 600. The pinion can be driven by a direct drive motor, or by a high accuracy gearbox coupled to a motor. When using a pinion, the backlash of the pinion to the main gear can be adjusted. This adjustment can be accomplished through the use of a lever arm screw adjustment.

It is also possible to rotate the magnet using a belt, for example, when continuously rotating MPI system 600.

Another approach to rotating the magnet is to use a hydraulic piston. A hydraulic piston is efficient at moving the magnet, but can require complex linkages in order to enable 180° or 360° rotation.

The present disclosure contemplates a number of ways of including or excluding components that make up a rotating gantry assembly for rotating an MPI system. The magnet is typically mounted to and rotates with the gantry, as rotation of FFL 140 is an aim of the rotating gantry assembly. In some implementations, other components such as an RF shielding system and RF receive subsystems are attached to the rotating gantry, and in other designs the RF shield and RF receiver subsystems remain stationary.

Figure 8:
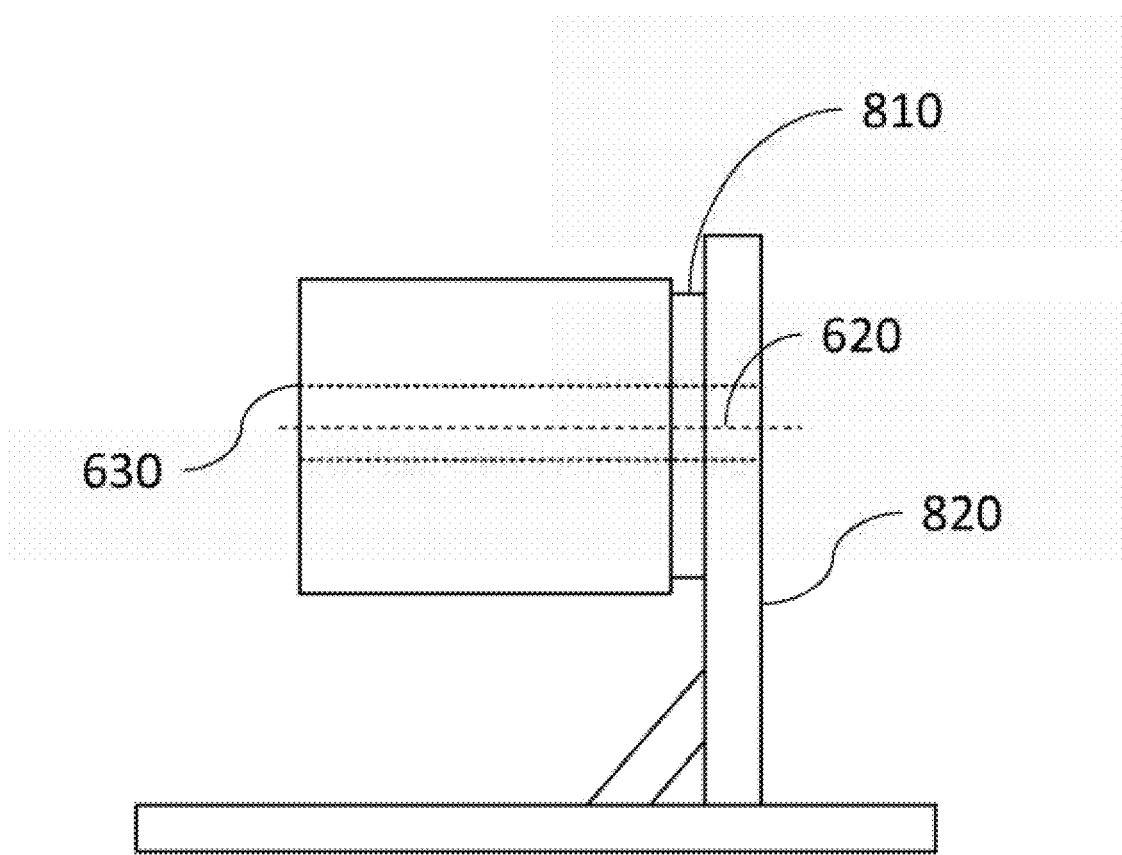
FIG. 8 is a diagram illustrating an example of an end bearing support for an MPI system in accordance with certain aspects of the present disclosure.

FIG. 8 is a diagram illustrating an end bearing support for an MPI system in accordance with certain aspects of the present disclosure. One approach to supporting a horizontal bore MPI system is to support the magnet from a single end. As shown in FIG. 8, there can be an end bearing assembly 810 that operatively couples MPI system 600 to a support gantry 820. In this implementation, the bore 630 and the rotation axis are centered on the end bearing assembly 810.

Figure 9:
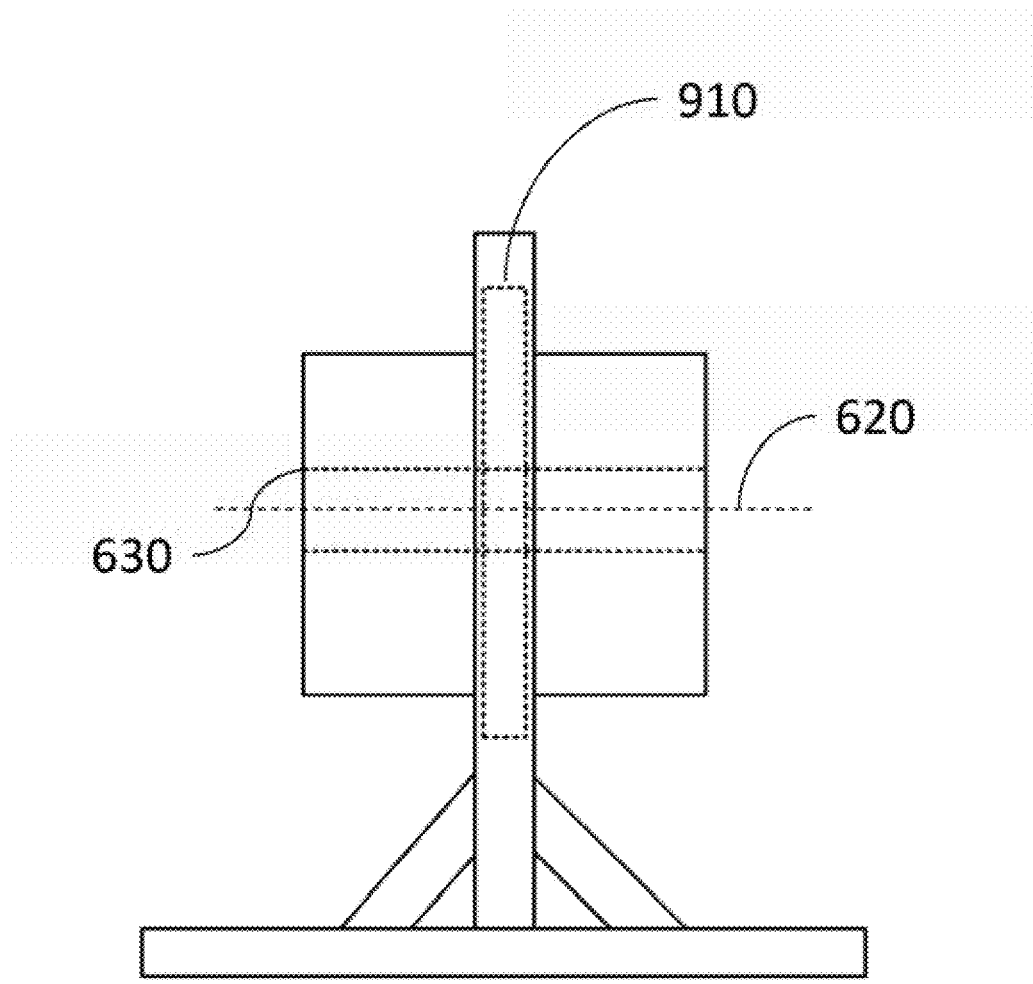
FIG. 9 is a diagram illustrating an example of a center bearing support for an MPI system in accordance with certain aspects of the present disclosure.

FIG. 9 is a diagram illustrating a center bearing support for an MPI system in accordance with certain aspects of the present disclosure. In some implementations, the magnet can also be inserted into a center bearing assembly 910, shown in FIG. 9. The center bearing assembly 910 can be close to the center of gravity of MPI system 600.

Figure 10:
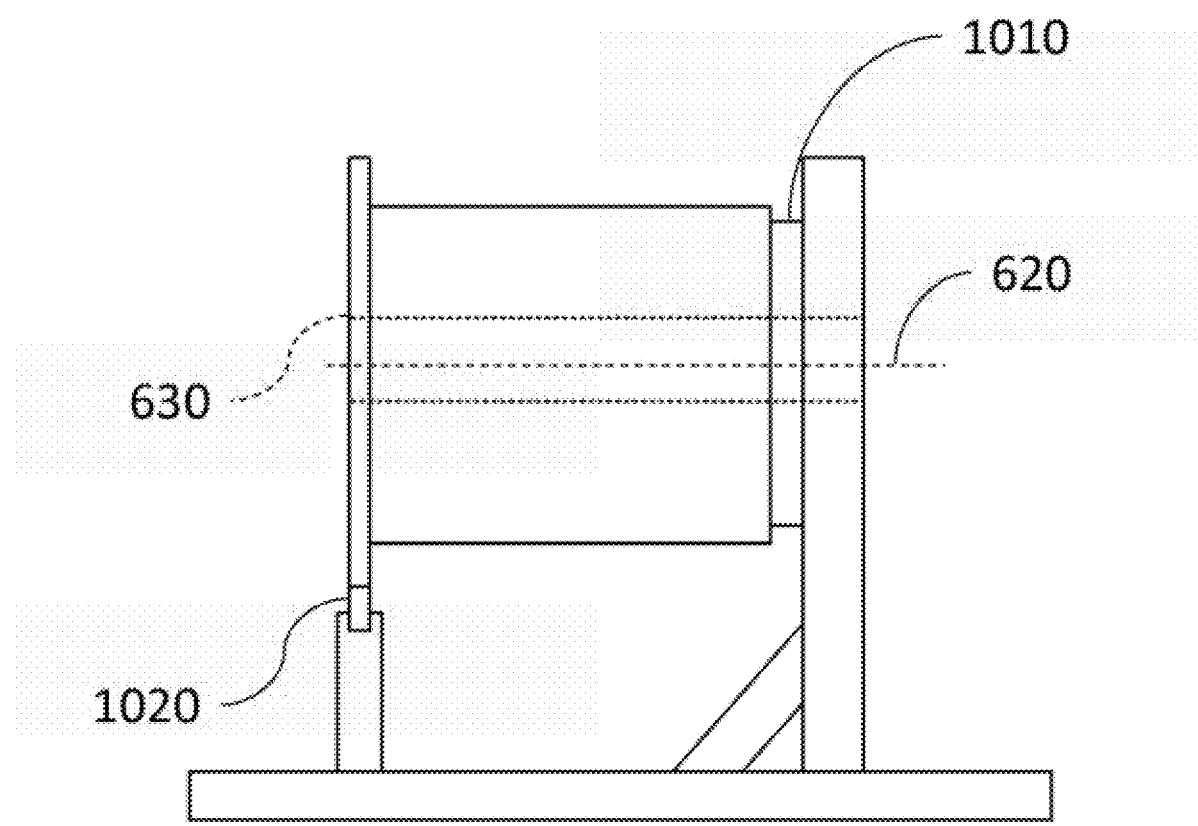
FIG. 10 is a side elevational view illustrating an example of a three bearing support for an MPI system in accordance with certain aspects of the present disclosure.
Figure 11:
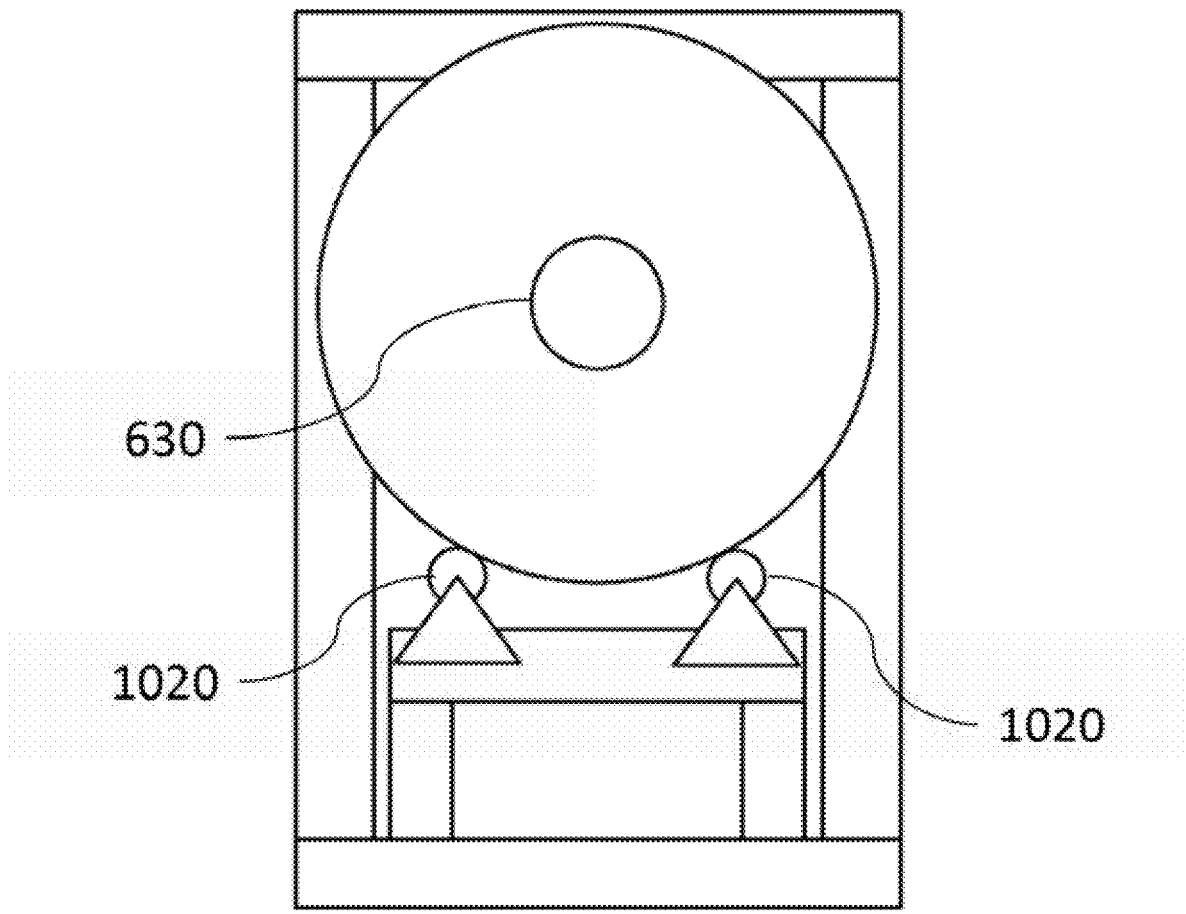
FIG. 11 is a front elevational view illustrating an example of a three bearing support for an MPI system in accordance with certain aspects of the present disclosure.

FIG. 10 is a side elevational view illustrating a three bearing support for an MPI system in accordance with certain aspects of the present disclosure. FIG. 11 is a front elevational view illustrating the three bearing support.

MPI system 600 can be supported from a first end at a first bearing assembly 1010 and stabilized by the addition of two second bearings assemblies 1020 to support a second opposing end of the MPI system. The bearings can press against a plate that is aligned such that it ensures that the centerline of the magnet is also the axis of the rotation. This may be done by attaching the plate to the magnet rotating gantry after manufacturing the magnet gantry. Preferably, the plate is capable of being separately aligned and attached in order to ensure accuracy in alignment of the plate with the rotation axis. Alternatively, the plate can be machined in place after manufacturing the rotating gantry to ensure that the outer diameter is concentric with the axis of rotation of the large bearing. The substantial weight of the magnet may make it such that the gantry and the support frame bend and ensure that the two small bearing assemblies remain in consistent contact with the round plate throughout the full rotation.

Following mounting of the magnet to the frame, the small bearing assemblies can be adjusted so that they contact the round plate. In an exemplary design, one may use bearings that can tolerate angular misalignment, such as self-aligning bearings, so that the contact patch is a line. An improved contact patch can prevent plastic deformation of the metal plate contact surface since the bearings support a substantial part of the load.

The large bearing can be designed to support the full weight of the magnet for safety during construction and shipping of the instrument. The two small bearings can be designed to be retracted during shipping to prevent vibration and shocks during shipping from indenting the edge of the round plate. Indentation of sufficient magnitude can negatively affect the magnet's ability to produce high-resolution images. To ensure safety of the magnet, shipping brackets may be added to the rotating plate and the rear of the gantry to limit motion during shipping in the three instrument axes and the rotation axis.

Figure 12:
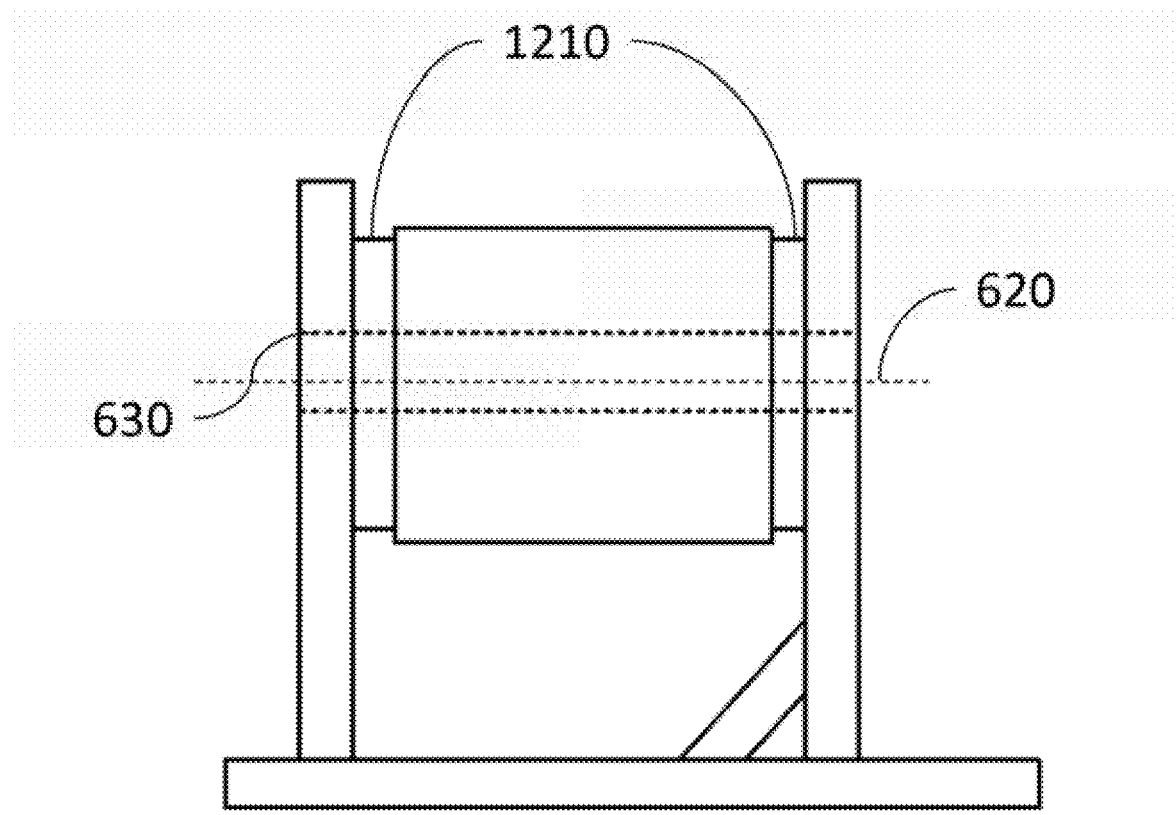
FIG. 12 is a diagram illustrating an example of two open bore bearing assemblies for an MPI system in accordance with certain aspects of the present disclosure.

An exemplary design of a rotating electromagnet is a magnet that is supported at both ends by bearing assemblies, as shown in FIG. 12. At the front of the magnet, the gantry, which contains the magnet and RF shielding, is supported by two smaller bearings that mate with a round plate. At the rear of the magnet, the gantry is supported by a single large bearing which has a clear bore 630. The RF shield box, which is mounted to the gantry, extends through the clear bore 630. At the rear of the magnet is a cable management assembly. The bearing assemblies can be adjusted up and down.

FIG. 12 is a diagram illustrating two open bore 630 bearing assemblies for an MPI system in accordance with certain aspects of the present disclosure. This alternative implementation includes two large bearing assemblies for a horizontal bore magnet, an example of which is shown in FIG. 12. This design may include the use of one standard bearing (e.g., a four point contact ball bearing), and one bearing that can accommodate angular misalignment, such as self-aligning bearings.

Figure 13:
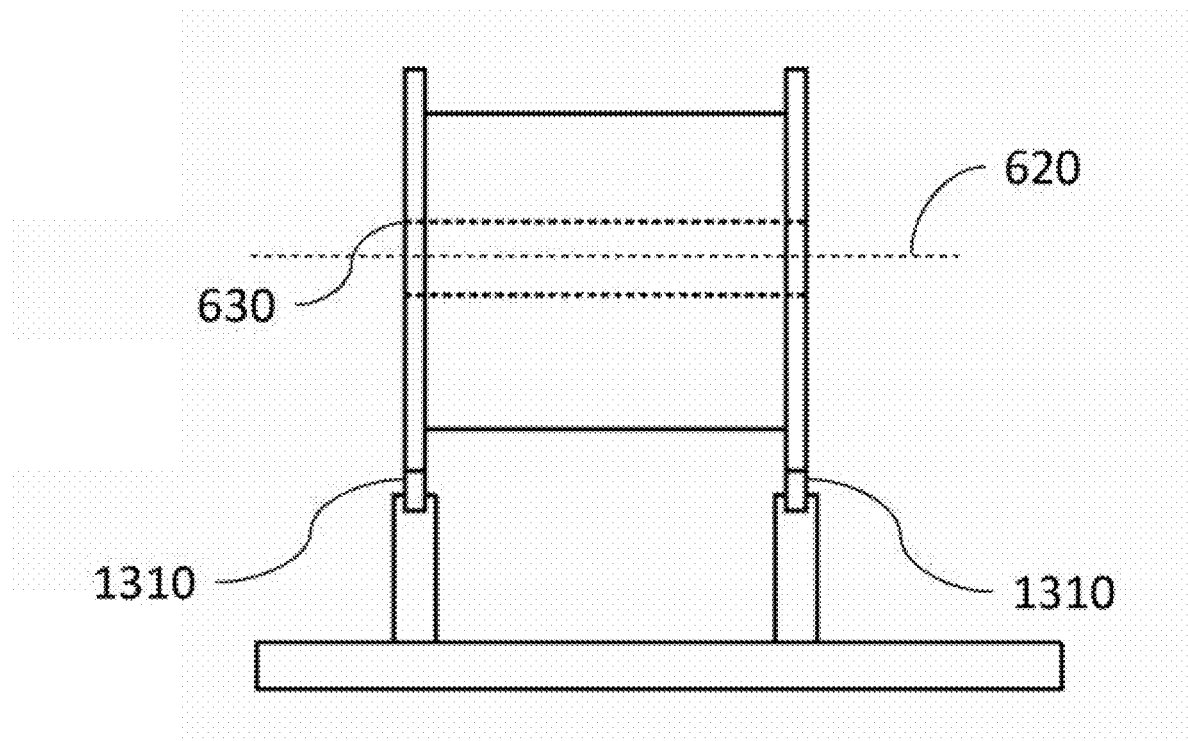
FIG. 13 is a diagram illustrating an example of multiple small bearing assemblies for an MPI system in accordance with certain aspects of the present disclosure.

FIG. 13 is a diagram illustrating multiple small bearing assemblies for an MPI system in accordance with certain aspects of the present disclosure. In yet another implementation, the magnet may be supported using three or four small bearing contact surfaces, an example of which is shown in FIG. 5. To prevent the magnet from running off the bearings, any number of (e.g., three or four) v-groove rollers and matching plates may be used on the magnet.

Figure 14:
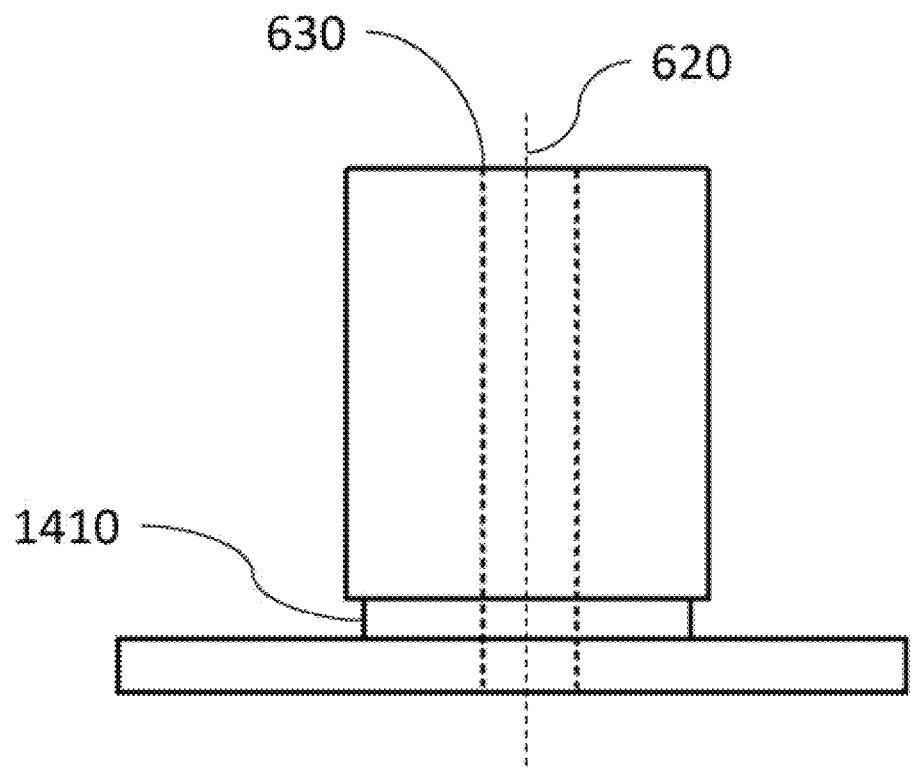
FIG. 14 is a diagram illustrating an example of a single bearing assembly for a vertical bore MPI system in accordance with certain aspects of the present disclosure.

FIG. 14 is a diagram illustrating a single bearing assembly for a vertical bore 630 MPI system in accordance with certain aspects of the present disclosure.

In some magnet designs, it is desirable for the magnet to rotate around a vertical sample 410. This could be the case for two unique scanner concepts including a human breast scanner (accessed from above), or a human brain scanner (accessed from below the magnet, e.g., a patient in a seated position 310). In these cases, the substantial weight of the magnet can be supported on a bearing assembly. An exemplary single bearing assembly 1410 for a vertical bore magnet is shown in FIG. 14.

Even with best efforts taken to ensure accurate control of the rotational position of the magnet assembly, additional encoders may be added to the gantry itself to provide direct measurement and feedback of the gantry position. Encoder devices for gantry position include printed encoder marks on the gantry itself, or monitoring of the gantry position using a rotary encoder mated to a round plate.

Figure 15:
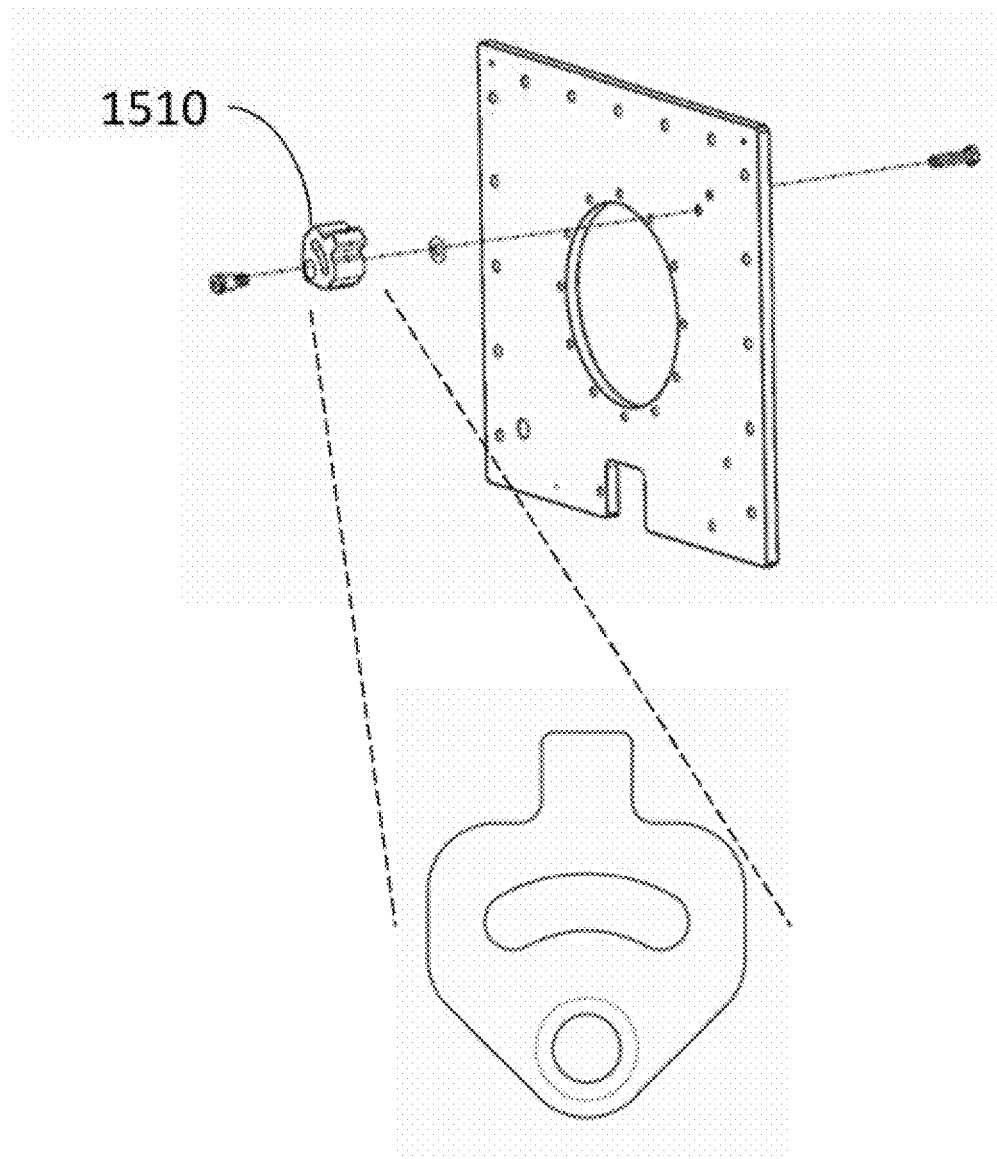
FIG. 15 is a diagram illustrating an example of a mechanical stop in accordance with certain aspects of the present disclosure.

FIG. 15 is a diagram illustrating a mechanical stop in accordance with certain aspects of the present disclosure.

The magnet preferably includes a mechanical stop 1510 for safety when the magnet has hard-wired connections to supporting equipment (amplifiers, water cooling, etc.). The hard stop may be designed in such a way that the magnet can still rotate 360 degrees. The hard stop engages with a post on the gantry after the gantry has been rotated beyond 360 degrees, thereby still enabling a full 360 degrees of movement. The stop can also incorporate a shock absorber to safely absorb the energy of the system during a fast stop utilizing the mechanical stop.

Figure 16:
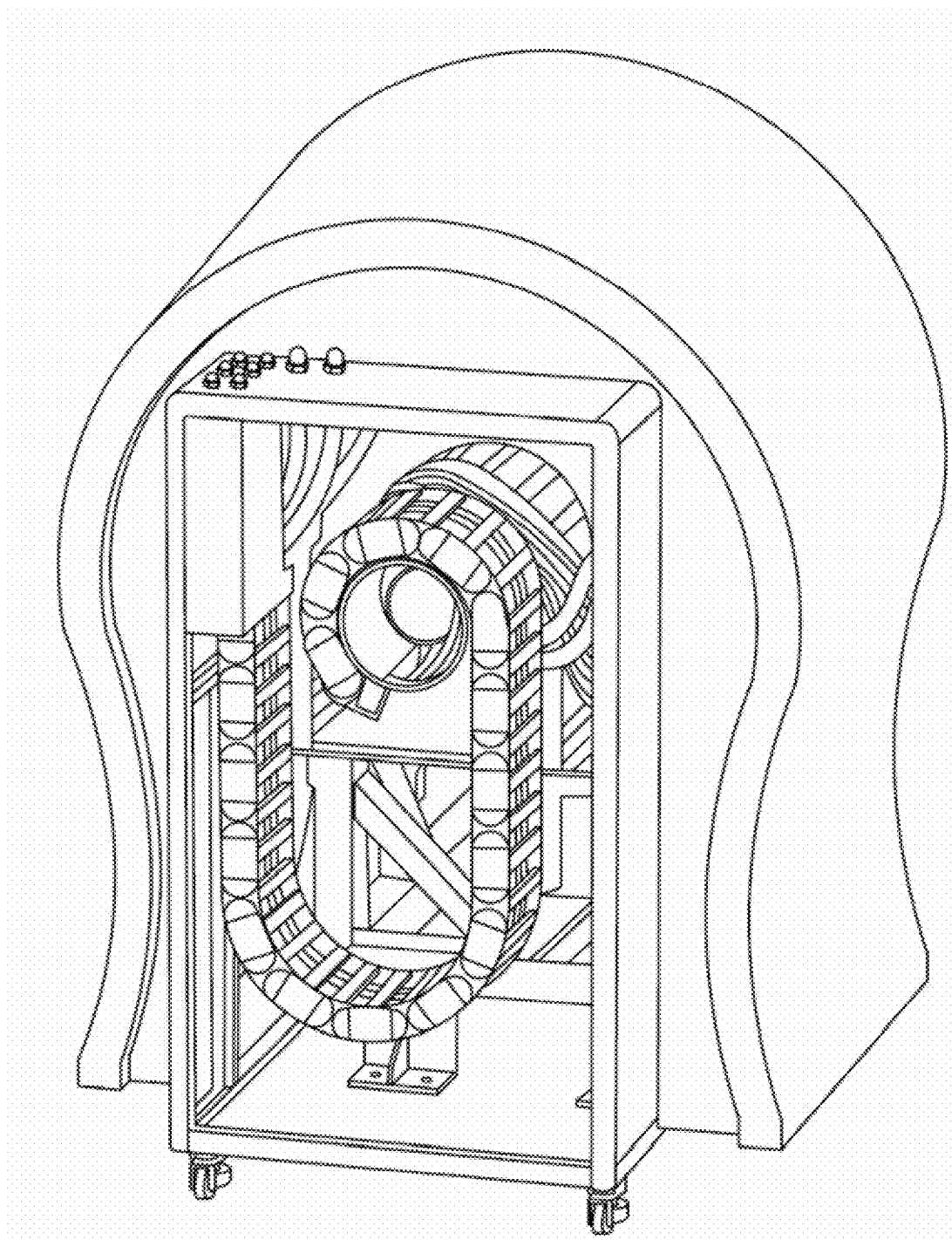
FIG. 16 is a diagram illustrating an example of a cable track for limited rotation in an MPI system in accordance with certain aspects of the present disclosure.

FIG. 16 is a diagram illustrating a cable track for limited rotation in an MPI system in accordance with certain aspects of the present disclosure. Here, we opt to support a limited rotation range using a cable spool. In a limited rotation system, we aim to manage the wire and hoses so that they spool safely and repeatedly with no kinking or binding. This can be done by mounting the wires and hoses in a cable carrier (e.g., IGUS, Inc.) and winding them on a spool. An exemplary design is shown in FIG. 16. In this exemplary design, cables and hoses can be rated for high flex usage. The exemplary design shown in FIG. 16 specifies a corrugated teflon water hose with a kevlar coating that is suitable for repeated flexing. The low noise electrical cables that carry the received signal may benefit from being constructed using low triboelectric noise wiring. Once the end of rotation is reached, the direction of rotation can be reversed.

A cable management system for a limited range rotational system (e.g., 360 degrees) can be one in which the cables associated with the magnet and other components of the gantry system are routed through the center of the bearing and out one end of rotating MPI system 600. The cables can then be guided along a windable track that has some flexibility to adapt to the winding of the cables as rotating MPI system 600 turns. The cables can then be mated with a stationary interface panel.

To realize continuous rotation of the gantry and associated subsystems, slip rings may be implemented. However, care must be taken as slip rings can introduce noise to MPI system 600 and compromise SNR. Specific design choices that may be considered include brushed slip rings, inductive and capacitive slip rings, liquid metal slip rings, fiber optic slip rings, and water slip rings. For example, high power low frequency magnet currents are well matched to brushed slip rings. The low power signal after the preamplifier can be more difficult to transmit to the console, and so multiple options exist to get the signal back while adding little noise. These include a low noise liquid metal slip ring (e.g., Mercotac, Inc.), RF upconversion and the use of capacitive slip rings or inductive slip rings, and digitization on the gantry and digital transmission to the console via optical or digital slip rings.

Of note is that cooling fluids (e.g., water, fluorinert, galden, or oil) may also need to be supplied to the magnet and the RF subsystems. There exist off-the-shelf slip rings (e.g., Dynamic Sealing Technologies, Inc.) capable of supplying sufficient cooling fluid. In an exemplary system, typical rotation speed would be approximately 0.5 rotations to 1 rotation per second, which would allow the imager to temporally resolve blood perfusion.

In embodiments where the magnet may rotate continuously or rotate through a large angle (e.g., 360 degrees), the routing of the cables and hoses through the system can be complex. For a large bearing system, the hoses and electrical wires are preferably routed through the center of the bearing. This routing is preferred so that the magnet is capable of rotating 360 degrees or continuously rotating without the wires binding with the magnet frame. An exemplary design that can be implemented with cables routing through the center of the bearing 1010 is shown in FIG. 10.

Figure 17:
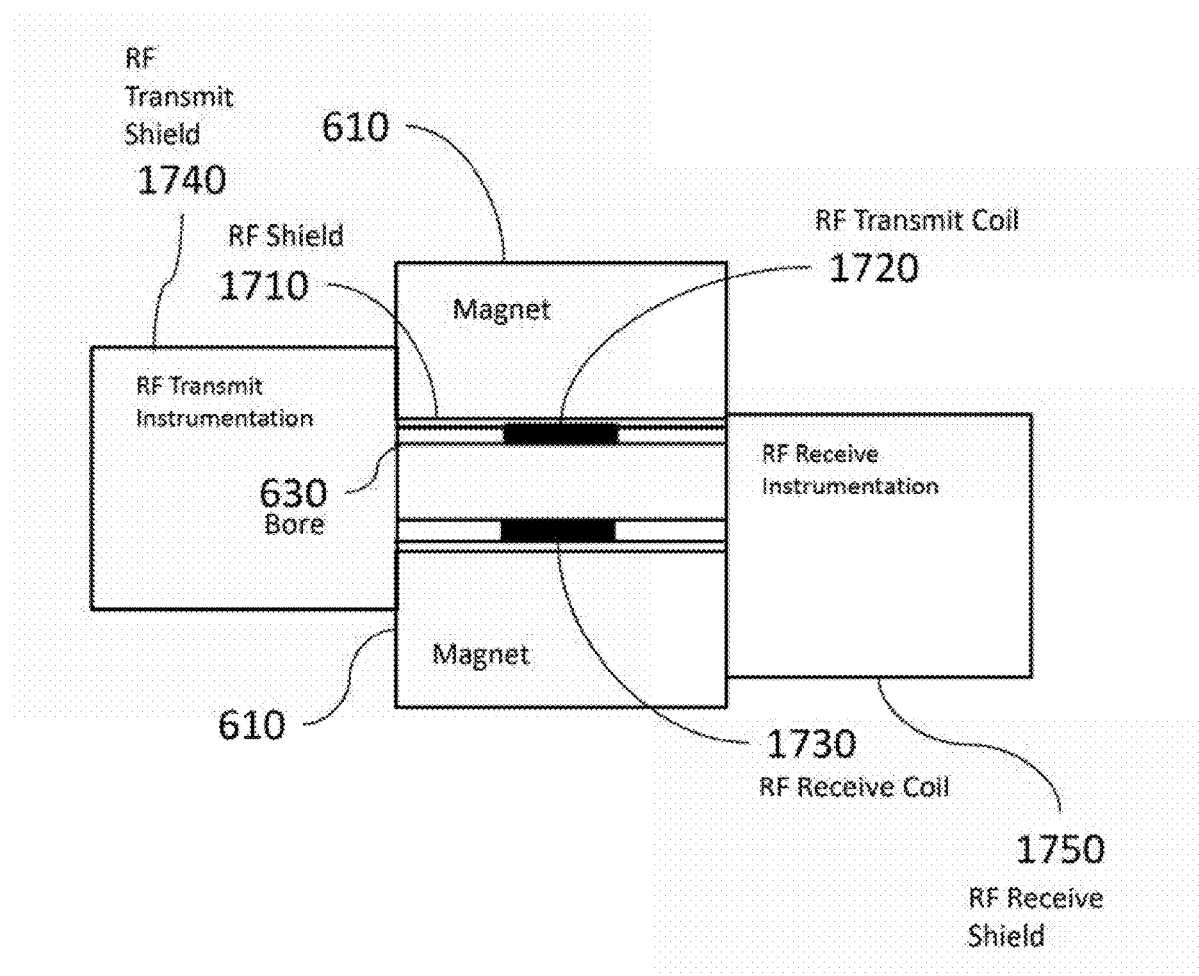
FIG. 17 is a diagram illustrating an example of a radio frequency (RF) shield in accordance with certain aspects of the present disclosure.

FIG. 17 is a diagram illustrating a radio frequency (RF) shield 1710 in accordance with certain aspects of the present disclosure. In some implementations, the bore 630 can include one or more RF transmit coils 1720 and one or more RF receive coils 1730. A radio frequency RF shield 1710 can be implemented to electrostatically and magnetically isolate the bore 630 from the external environment. For self-shielding MPI systems, (e.g., not enclosed in a larger shield room or shield enclosure), an RF shield 1710 can be integrated. In an exemplary design, the RF shield 1710 extends through the magnet, from the front to the rear. The front of RF shield 1710 holds the RF receivers, and the rear of RF shield 1710 includes the RF transmit filters that provide, for example, high-pass, low-pass, or bandpass filtering of transmitted RF.

In some implementations, RF shield 1710 can be mounted to rotate with the MPI system. It is contemplated that any part of RF shield 1710 can be mounted to the MPI system. For example, RF shield 1710 can include RF shield 1710 (surrounding some or all of bore 630), RF transmit shield 1740 (shielding the RF transmit filter(s)), or RF receive shield 1750 (shielding the RF receive filter(s) and preamplifier(s)). Any combination of the above RF shielding can be implemented. Similarly, any combination of the above RF shielding can be mounted to rotate with the MPI system while other portions of the RF shielding remain stationary and do not rotate.

With rotating MPI system 600, projections can be acquired while rotating the mechanically-rotatable magnet 610. In some implementations, acquisition of projections can include, for example, rotating the mechanically-rotatable magnet 610 to orient the field free line at various angles, positioning FFL 140 at a number of positions at the plurality of angles, and controlling the excitation source and RF detector to acquire signals from magnetic particles in a sample 410 within the field free line.

The angles at which the magnet may be oriented can be any number and value of angles that MPI system 600 is capable of rotating to. In some implementations, for example, if it is desired or required to utilize a large number of angles, the angles can include, for example, 50, 100, 200, or 500 angles spread over a 360° span of rotation of MPI system 600. The number and value of the angles can be, for example, predefined (e.g. stored in a computer data file), selected by a user at a user interface, calculated by a control system to provide a desired set of angles for acquiring a particular image at a particular resolution, etc. Depending on the approach to imaging the sample 410, imaging can be performed with different scanning or rotation modes. Some exemplary scanning modes that can provide coverage of a sample 410 are described below.

Figure 18:
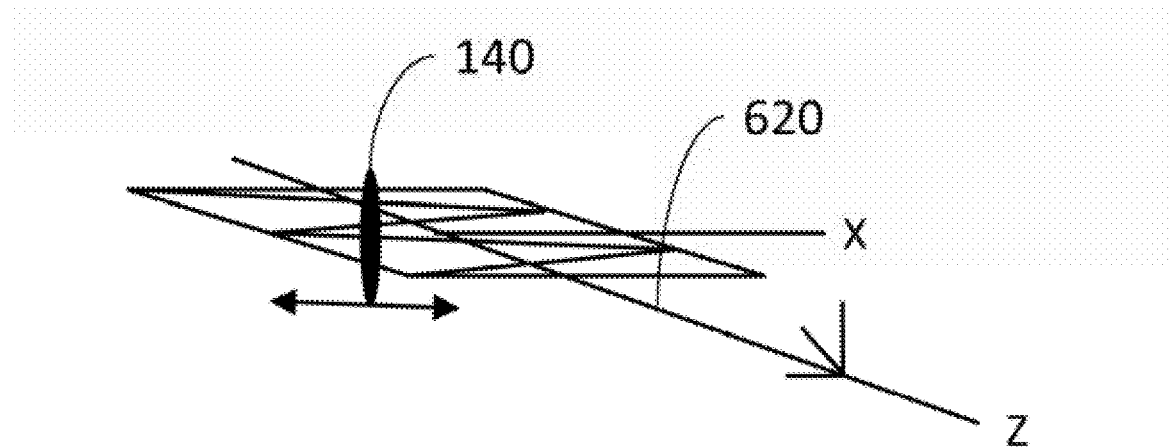
FIG. 18 is a diagram illustrating an example of step-scan imaging in MPI system in accordance with certain aspects of the present disclosure.

FIG. 18 is a simplified diagram illustrating an example of step-scan imaging in an MPI system in accordance with certain aspects of the present disclosure. A step-scan approach acquires projections at a number of angles by rotating the MPI system, fixing the mechanically-rotatable magnet 610 at an angle, and then positioning FFL 140 at a number of different positions to acquire the projections. This process may then be repeated by rotating the magnet to another angle, similarly acquiring projections, and so on.

Figure 19:
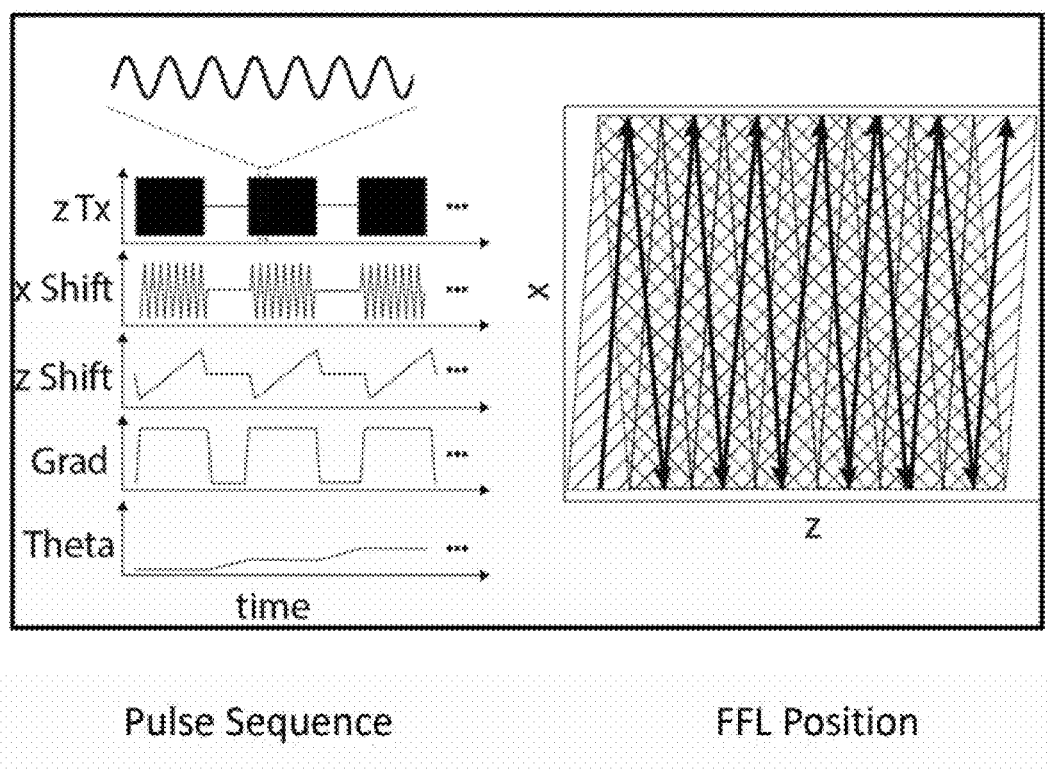
FIG. 19 is a diagram illustrating an example of a pulse sequence for step-scan imaging in MPI system in accordance with certain aspects of the present disclosure.

FIG. 19 is a diagram illustrating an example of a pulse sequence for step-scan imaging in MPI system 600 in accordance with certain aspects of the present disclosure. This pulse sequence is similar to that shown in FIG. 2, however, the bottom plot shows the progression of the angle of the MPI system 600 over time. As shown, the MPI system is at a first angle, projections are acquired, then imaging halts or pauses while the MPI system is rotated to the next angle, where additional projections are acquired.

The exemplary positions of FFL 140 are shown in the right portion of FIG. 19. As previously stated, an X-Z plane in the exemplary system rotates around the Z axis with mechanically-rotatable magnet 610. Accordingly, the positions of FFL 140 as shown are similar to those shown for the stationary case. However, acquiring projections at each angle can generate data that an image reconstruction system can utilize to generate an image based on the projections, including three-dimensional images.

In some implementations, an image reconstruction system can also be configured to create a projection image from a plurality of projections acquired at a fixed angle.

Figure 20:
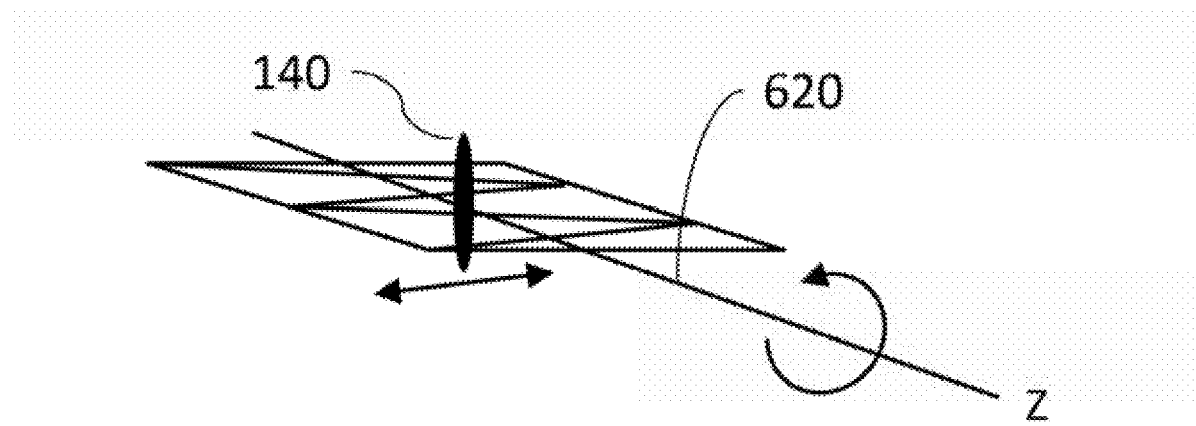
FIG. 20 is a diagram illustrating an example of continuous rotation imaging in an MPI system in accordance with certain aspects of the present disclosure.

FIG. 20 is a simplified diagram illustrating an example of an MPI system utilizing continuous rotation in accordance with certain aspects of the present disclosure. As shown in FIG. 20, in some implementations, positioning FFL 140 at different positions can occur while the mechanically-rotatable magnet 610 is rotating.

Continuous rotation implementations may include changes in rotational speed, for example speeding up or slowing down, while still rotating the MPI system and acquiring projections.

Figure 21:
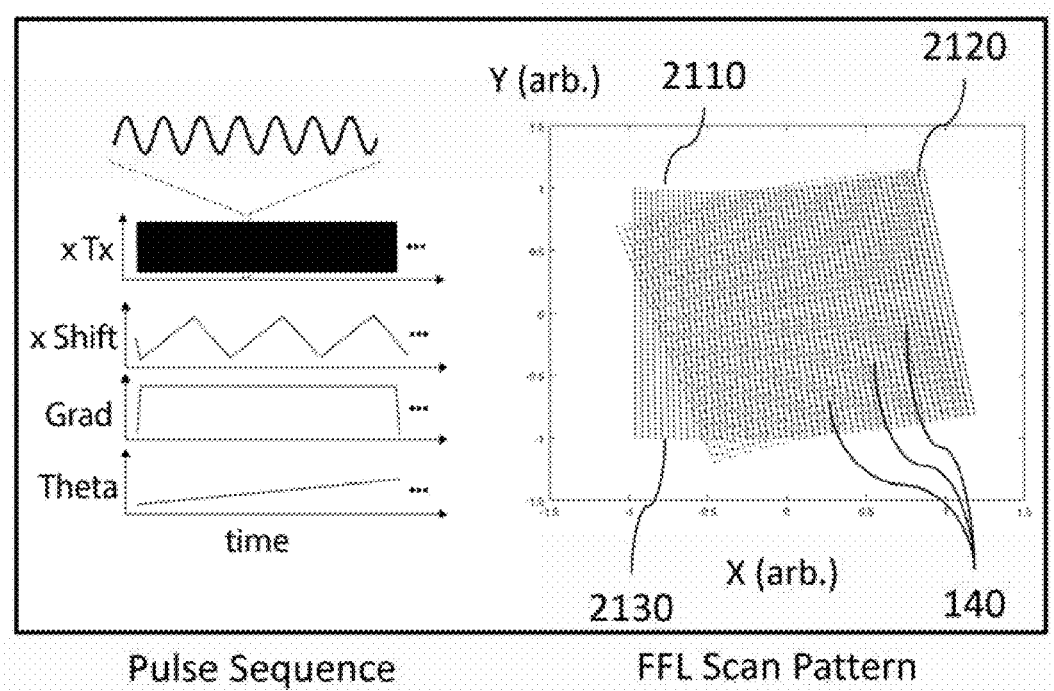
FIG. 21 is a diagram illustrating an example of a pulse sequence for continuous rotation imaging in accordance with certain aspects of the present disclosure.

FIG. 21 is a diagram illustrating a pulse sequence for continuous rotation imaging in accordance with certain aspects of the present disclosure. This pulse sequence is similar to the pulse sequence shown in FIG. 19, however, instead of the angle being stepped from one value to another, the angle is continuously varied.

The plot on the right side of FIG. 21 shows a representation of a sequence of FFLs (e.g., simplified as lines in the X-Y plane) as the position of the FFL is shifted in X and continuously rotated in angle. The series of lines represent the FFL over a sweep from left to right (shown by the solid lines 2110), to a reversal point 2120, and a sweep from right to left (shown by the dashed lines 2130). Considering only the sweep left to right, it can be seen that the solid lines 2110 gradually rotate from vertical (e.g., along with the Y axis) to an angle of about 10° from vertical at reversal point 2120. Here, FFL 140 is being rotated by virtue of the rotation of MPI system 600. At reversal point 2120, the direction of scanning changes and FFL 140 is scanned right to left. However, the rotation of FFL 140 continues to change the angle of FFL 140, and at the end of the right to left scan, FFL 140 is at an angle of about 20° from vertical. Again, at each position and angle of FFL 140, projections can be acquired and used to reconstruct an image. Accordingly, this can allow for the acquisition of projections for reconstructing two-dimensional images such as slices. Three-dimensional images (e.g. slabs) can also be generated when the position or shape of FFL 140 has some extent along rotation axis 620.

Figure 22:
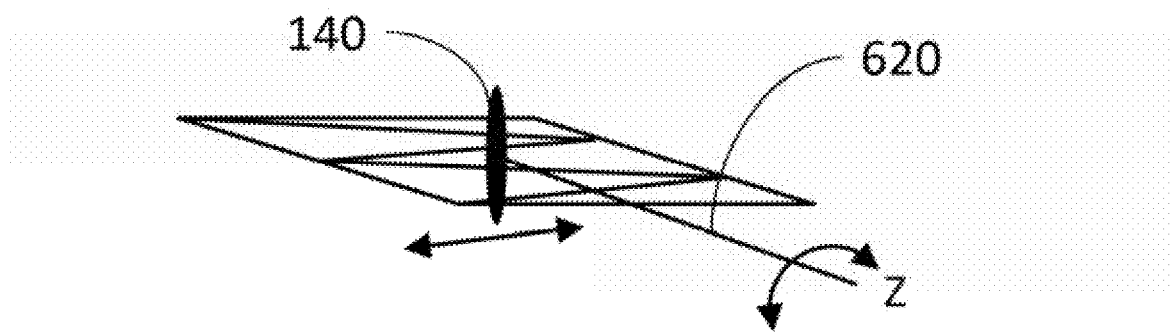
FIG. 22 is a diagram illustrating an example of back-and-forth imaging in an MPI system in accordance with certain aspects of the present disclosure.

For continuous imaging embodiments where the MPI system is not configured for continuous rotation, the present disclosure contemplates that imaging can take place when the rotation of the magnet includes reversing the rotation direction during the acquisition of the plurality of projections. FIG. 22 is a simplified diagram illustrating an example of back-and-forth imaging in an MPI system in accordance with certain aspects of the present disclosure. As in prior implementations, the field free line is moved through a number of different positions, and is moving through these positions, while the magnet is rotating. At some point, the magnet rotation direction can reverse. Reversal may happen after a rotation of approximately 360°, or at some other angle.

Figure 23:
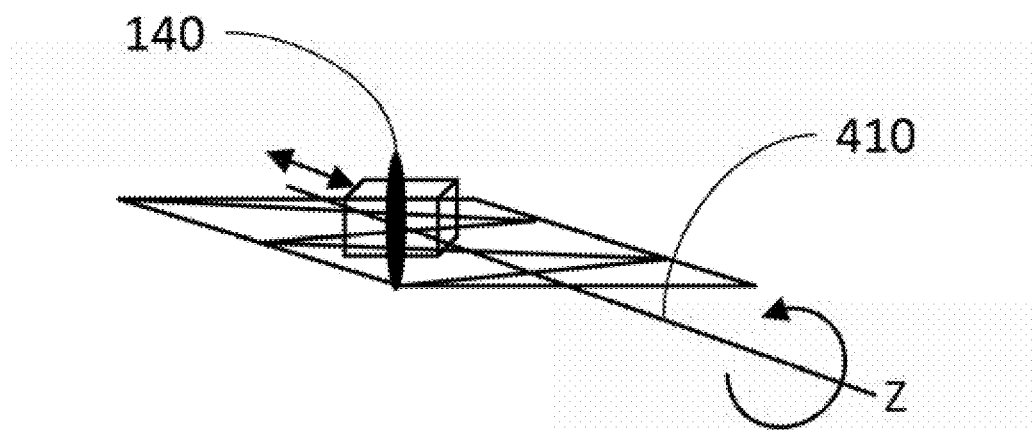
FIG. 23 is a diagram illustrating an example of spiral imaging in an MPI system in accordance with certain aspects of the present disclosure.

FIG. 23 is a simplified diagram illustrating imaging in an MPI system in accordance with certain aspects of the present disclosure. In one implementation, spiral imaging combines the previously described rotation of the magnet while acquiring projections, along with the control system being further configured to move the sample through the bore of the magnet during rotation of the magnet. Is also contemplated that projections can be acquired, as previously discussed, and, after a full set has been acquired, the control system can move the sample along the axis of the bore, and repeat the acquisition of projections. With either of the data acquisition methods described here, the image reconstruction system may be configured to generate a three-dimensional or volumetric image.

Figure 24:
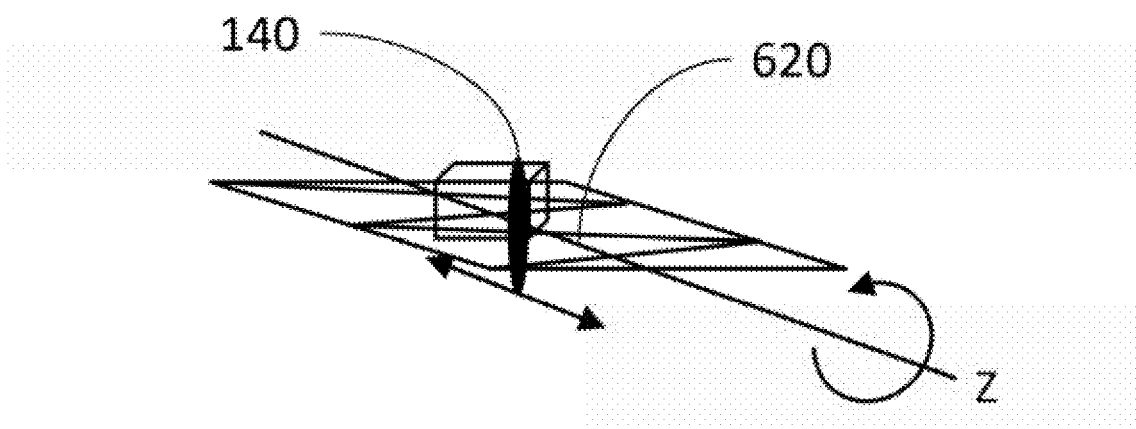
FIG. 24 is a diagram illustrating an example of spiral imaging by moving the FFL in an MPI system in accordance with certain aspects of the present disclosure

In another implementation, depicted in the simplified diagram of FIG. 24, the previously described rotation of the magnet while acquiring projections may be combined with a configuration of the control system that allows for translation of the FFL along the axis of the bore, effected by the magnet itself, and not by physical movement of a portion of the system. This translation of the FFL may be done during rotation of the magnet, or only after a full-rotation dataset is acquired (in step-like fashion). The data acquired in such implementations can likewise be utilized by the image reconstruction system to create a three-dimensional or volumetric image.

In an exemplary embodiment that allows repetitive fast imaging over a thin slice field-of-view, the magnet is rotated while projections are acquired and the positions of the field free line vary only in the one direction. For example, FFL positions may be varied only in the X direction, and the excitation source may only excite or move the FFL in the X direction as well. This method of data acquisition may be particularly useful for rapid perfusion or functional MPI imaging of a thin slice of a subject.

In another embodiment, the magnet is rotated while projections are acquired and the positions of the field free line are varied in two directions. For example, FFL positions may be varied in both the X and Z directions, and the excitation source may excite or move the FFL in both the X and Z directions as well.

In an alternative embodiment, shim magnet(s) may be used to counteract the normal flux distribution around the main magnet and thereby reshape the FFL into different forms, for example, into an approximation of a field-free point, or into an ellipsoidal field-free region. Utilization of such alternatively shaped FFLs (such as an ellipsoid) to acquire projections during magnet rotation may enable beneficial slab-type imaging.

As disclosed herein, it is contemplated that the methods and systems described herein can be combined to perform many types of two and three dimensional imaging. The simplified examples presented herein are not intended to be limiting or exclusive of any combinations of the disclosed features.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims.

The invention claimed is:

1. A Magnetic Particle Imaging (MPI) system comprising:
a mechanically-rotatable magnet configured to generate a magnetic field including a field free line;
an excitation source;
an RF detector;
an RF shield surrounding some or all of a bore of the MPI system;
a control system configured to acquire a plurality of projections at a plurality of angles, the acquiring comprising:
rotating the mechanically-rotatable magnet to orient the field free line at the plurality of angles;
positioning the field free line at a plurality of positions at the plurality of angles; and
controlling the excitation source and RF detector to acquire signals from magnetic particles in a sample within the field free line at the plurality of positions; and
an image reconstruction system configured to generate an image based at least on the plurality of projections,
wherein the RF shield is configured to remain stationary during the rotating of the mechanically-rotatable magnet.

2. The system of claim 1 wherein positioning the field free line at a plurality of positions occurs with the mechanically-rotatable magnet fixed at an angle.

3. The system of claim 2 wherein the image reconstruction system is further configured to create the image from a plurality of projections acquired at a fixed angle.

4. The system of claim 1 wherein positioning the field free line at a plurality of positions occurs while the mechanically-rotatable magnet is rotating.

5. The system of claim 4 wherein rotating the mechanically-rotatable magnet includes reversing rotation direction during the acquiring of the plurality of projections.

6. The system of claim 4 wherein the control system is further configured to move the sample through a bore of the mechanically-rotatable magnet during the acquiring.

7. The system of claim 6 wherein the image reconstruction system is configured to generate a three-dimensional image.

8. The system of claim 1 wherein the control system is further configured to move the sample through a bore of the mechanically-rotatable magnet and acquire an additional plurality of projections at another plurality of angles.

9. The system of claim 8 wherein the image reconstruction system is configured to generate a three-dimensional image.

10. The system of claim 1 wherein the control system is further configured to electronically move the free field line along a rotation axis of the mechanically-rotatable magnet and acquire an additional plurality of projections at another plurality of angles.

11. The system of claim 10 wherein the image reconstruction system is configured to generate a three-dimensional image.

12. The system of claim 1 wherein positioning the field free line at a plurality of positions is accomplished at least by the mechanically-rotatable magnet generating a modified magnetic field.

13. The system of claim 1 wherein positioning the field free line in a plurality of positions includes varying the position of the field free line only in the X direction with a shifting magnet and an excitation magnet.

14. The system of claim 1 wherein positioning the field free line in a plurality of positions includes varying the position of the field free line in both the X direction and in the Z direction with at least one magnet and with at least one excitation magnet.

15. The system of claim 1 further comprising at least one shim magnet configured to alter the magnetic field.

16. The system of claim 15 wherein alteration of the magnetic field causes a widening of the field free line.

17. The system of claim 1 wherein the control system is further configured to set an excitation field vector that specifies a strength and direction of a magnetic field generated by the excitation source.

18. The system of claim 1 wherein the mechanically-rotatable magnet is coupled to one or more slip rings to allow for continuous rotation of the mechanically-rotatable magnet.

19. The system of claim 18, wherein the one or more slip rings include one or more of: a capacitive slip ring, an inductive slip ring, an optical slip ring, or a digital slip ring.

20. The system of claim 1 wherein the excitation source includes a transmit coil and the transmit coil does not rotate with the mechanically-rotatable magnet.

21. The system of claim 1 wherein the RF detector includes a receive coil and the receive coil does not rotate with the mechanically-rotatable magnet.

22. A computer program product comprising a non-transient, machine-readable medium storing instructions which, when executed by at least one programmable processor, cause the at least one programmable processor to perform operations comprising:
　causing an MPI system comprising:
　　a mechanically-rotatable magnet;
　　an excitation source;
　　an RF detector;
　　an RF shield surrounding some or all of a bore of the MPI system;
　　a control system; and
　　an image reconstruction system, to perform operations comprising:
　　　generating, by the mechanically-rotatable magnet, a magnetic field including a field free line;
　　　acquiring, with the control system, a plurality of projections at a plurality of angles, the acquiring comprising:
　　　　rotating the mechanically-rotatable magnet to orient the field free line at the plurality of angles;
　　　　positioning the field free line at a plurality of positions at the plurality of angles; and
　　　　controlling the excitation source and RF detector to acquire signals from magnetic particles in a sample within the field free line at the plurality of positions; and
　　　generating, with the image reconstruction system, an image based at least on the plurality of projections,
　　wherein the RF shield is configured to remain stationary during the rotating of the mechanically-rotatable magnet.

* * * * *